(12) United States Patent
Stajic et al.

(10) Patent No.: US 9,120,877 B2
(45) Date of Patent: Sep. 1, 2015

(54) SULFATED POLYSACCHARIDE COMPOUND AND THE PREPARATION AND USE THEREOF

(75) Inventors: Vladimir Stajic, Alexandria (AU); Norman William Cheetham, Alexandria (AU); Alan Bell, Alexandria (AU)

(73) Assignee: PARNELL TECHNOLOGIES PTY LTD (AU)

( * ) Notice: Subject to any disclaimer, the term of this patent is extended or adjusted under 35 U.S.C. 154(b) by 702 days.

(21) Appl. No.: 13/002,363

(22) PCT Filed: Oct. 8, 2008

(86) PCT No.: PCT/AU2008/001481
§ 371 (c)(1),
(2), (4) Date: Jun. 24, 2011

(87) PCT Pub. No.: WO2010/000013
PCT Pub. Date: Jan. 7, 2010

(65) Prior Publication Data
US 2011/0251154 A1    Oct. 13, 2011

(30) Foreign Application Priority Data

Jul. 4, 2008 (AU) .............................. 2008903436

(51) Int. Cl.
| | | |
|---|---|---|
| *A61K 31/737* | (2006.01) | |
| *C08B 37/00* | (2006.01) | |
| *C07H 11/00* | (2006.01) | |
| *C07H 13/02* | (2006.01) | |

(52) U.S. Cl.
CPC ............ *C08B 37/0057* (2013.01); *C07H 11/00* (2013.01); *C07H 13/02* (2013.01); *C08B 37/0003* (2013.01)

(58) Field of Classification Search
USPC .......................................... 514/54; 536/116
See application file for complete search history.

(56) References Cited

U.S. PATENT DOCUMENTS

| | | | | |
|---|---|---|---|---|
| 2,689,848 A | * | 9/1954 | Husemann et al. | 536/118 |
| 2,959,583 A | * | 11/1960 | Doczi | 536/20 |
| 4,713,373 A | * | 12/1987 | Bayol et al. | 514/54 |
| 4,814,437 A | * | 3/1989 | de Belder et al. | 536/18.7 |
| 5,180,715 A | | 1/1993 | Parsons | |
| 5,459,257 A | * | 10/1995 | Shoji et al. | 536/118 |
| 5,646,130 A | | 7/1997 | Shi | |
| 6,828,309 B2 | | 12/2004 | Striker | |
| 7,067,144 B2 | | 6/2006 | Demopulos et al. | |
| 2007/0243218 A1 | | 10/2007 | Ellinghuysen et al. | |

FOREIGN PATENT DOCUMENTS

| | | |
|---|---|---|
| EP | 0406685 A1 | 1/1991 |
| WO | 98/42754 A2 | 10/1998 |
| WO | 2007123800 A2 | 11/2007 |
| WO | 2009047699 A1 | 4/2009 |

OTHER PUBLICATIONS

NTP Executive Summary Data, 1990, pp. 1-28.*
Raveux et al. "Study of sulfuric polyesters of natural xylans extracted from beechwood, I.—Composition and general structure". (Bull. Soc. Chim. Fra.) pp. 2744-2749, vol. 33, No. 9, 1966.
Zhao et al. "Facile synthesis of the heptasaccharide repeating unit of O-deacetylated GXM of C. neoformans serotype B". (Bioorganic & Medicinal Chemistry) pp. 121-130. vol. 13, 2005.
World IP Organization. "International Search Report"/ PCT/AU2008/001481, Applicant: Parnell Laboratories (Aust) Pty Ltd, Mailed: Nov. 25, 2008.

* cited by examiner

*Primary Examiner* — Ganapathy Krishnan
(74) *Attorney, Agent, or Firm* — K&L Gates LLP; Louis C. Culman; Robert W. Winn

(57) ABSTRACT

The present invention relates to a sulfated polysaccharide compound and the preparation and use thereof, and in particular to a narrow distribution low molecular weight, highly sulfated pentosan (in this instance a xylan) referred to as glucuronoxylan sulfate (GXS). The invention has been developed primarily for use in the treatment of various clinical conditions. However, it will be appreciated that the invention is not restricted this particular field of use.

11 Claims, 21 Drawing Sheets

| | Unfractionated | 0-40% | 40-45 | 45-50 | 50-55 | 55-60 | 60-65 | 65-70 |
|---|---|---|---|---|---|---|---|---|
| %S | 18 | 18.1 | 18.2 | 18.5 | 18.4 | 17.8 | 16.9 | 17.1 |
| Yield %weight | | 9.2 | 31.7 | 13.7 | 13.6 | 9.4 | 7.1 | 5.8 |
| Mp | 3294 | 7342 | 4204 | 2654 | 2160 | 1829 | 1615 | 1528 |
| | %weight | | | | | | | |
| >10k | 4.67 | 22 | 5.17 | 1.35 | 0.62 | 0.34 | 0.13 | 0.03 |
| 9-10k | 0.62 | 3.5 | 1.36 | 0.4 | 0.18 | 0.12 | 0.05 | 0.01 |
| 8-9k | 0.89 | 4.48 | 1.96 | 0.61 | 0.27 | 0.18 | 0.08 | 0.02 |
| 7-8k | 1.35 | 5.84 | 2.98 | 1 | 0.45 | 0.29 | 0.14 | 0.03 |
| 6-7k | 2.26 | 7.78 | 4.83 | 1.81 | 0.82 | 0.52 | 0.27 | 0.06 |
| 5-6k | 3.94 | 10.03 | 8.02 | 3.54 | 1.69 | 1 | 0.58 | 0.15 |
| 4-5k | 7.22 | 12.08 | 13.3 | 7.56 | 4.01 | 2.21 | 1.39 | 0.46 |
| 3-4k | 13.74 | 13.22 | 21 | 17.67 | 11.77 | 6.63 | 4.18 | 2 |
| 2-3k | 27.59 | 13.29 | 26.5 | 38.5 | 38.23 | 29.93 | 20.76 | 15.14 |
| 1.5-2k | 22.29 | 5.23 | 10.4 | 20.2 | 30.49 | 38.88 | 38.56 | 38.72 |
| <1.5k | 15.42 | 2.53 | 4.51 | 7.37 | 11.47 | 19.91 | 33.87 | 43.39 |

SULFATED POLYSACCHARIDE COMPOUND AND THE PREPARATION AND USE THEREOF

FIELD OF THE INVENTION

The present invention relates to a sulfated polysaccharide compound and the preparation and use thereof, and in particular to a narrow distribution low molecular weight, highly sulfated pentosan (in this instance a xylan) referred to as glucuronoxylan sulfate (GXS).

The invention has been developed primarily for use in the treatment of various clinical conditions. However, it will be appreciated that the invention is not restricted this particular field of use.

COPYRIGHT NOTICE

This document is subject to copyright. The reproduction, communication and distribution of this document is not permitted without prior consent from the copyright owner, other than as permitted under section 226 of the Patents Act 1990.

Problems of the Prior Art

Under-Sulfation

Highly sulfated (sulfate esters) glycans and glycosaminoglycans form a significant therapeutic class of pharmaceuticals in human and veterinary medicine. Sulfate esters demonstrate a broad range of clinical utility in treating various conditions including osteoarthritis, myocardial ischaemia, interstitial cystitis, cancer, and the control and treatment of virus diseases, including human immunodeficiency virus and other retroviruses.

Pentosan polysulfate has been used in pharmaceutical formulations to treat osteoarthritis, as an anticoagulant or for other conditions such as interstitial cystitis, transmissible spongiform encephalopathy (TSE) and immunodeficiency virus (such as HIV/AIDS or Feline Immunodeficiency Virus (FIV)) in mammals, such as humans, food-producing and companion animals (such as feline, canine and equine). Pentosan polysulfate may also be used to treat haematomas, haemorrhoids, frostbite, burns, and multiparameter illnesses such as thrombosis and atherosclerosis.

Sulfate esters, including heparin, dextran sulfate and PPS are semisynthetic. Their derivation and synthesis have long proved to be very challenging, with production outcomes being highly variable. This has translated to inconsistent clinical outcomes. While there are currently no reported clinical trials looking at differences in clinical outcomes of osteoarthritis treatment using more homogenous and more highly sulfated PPS compared with low sulfated PPS, anecdotal evidence suggests variability in clinical outcome of low sulfated PPS. There are two main chemical reasons that might be behind variability of outcome:

(a) PPS with inconsistent molecular weight ranges; and
(b) PPS with a high variation in the degree of sulfation (14-17%).

Nevertheless, U.S. Pat. No. 4,713,373 supports the claim that fractions of glycan chains such as PPS with greater degrees of sulfation will have much better efficacy than those with lower sulfation. In relation to heparin (a glycosaminoglycan), it is known that the type and position of sulfate groups as well as the level of sulfation are important for efficacy.

The refinement of the glycan or glycosaminoglycan molecule (to the development, for example, of low molecular weight heparins) has been well documented as resulting in the development of molecules with greater consistency and predictability in clinical outcomes. However, in practice, it has proved difficult to achieve a consistently high level of sulfation at consistent positions along the chain and in a low molecular weight range. To date no-one has looked at the importance of the type and location of the sulfate groups or distinguished the chemical structure of the PPS molecule produced by one manufacturing process from that produced by another. Also, the degree of sulfation within known PPS formulations can vary widely, which can also lead to variability in clinical efficacy.

Pentosan polysulfate as free acid or in the salt form (typically with inorganic cations such as sodium or calcium) is described in the prior art as a mixture of semi-synthetic polysulfated oligosaccharides, generally obtained from beechwood xylan. Pentosan polysulfate consists of sulfated linear 1-4 conjugated beta-D-xylopyranose units and has 4-O-methyl-D-glucuronic acid randomly attached on every eight to ten xylose units (on average).

The typical number of xylose units in a PPS mixture reported in the prior art has been between six and thirty. PPS mixtures currently present on the market (when in the form of sodium salt at all $SO_3^-$ groups) typically contain 15 to 17% sulfation. While the prior art describes degrees of sulfation from 15 to 20%, it is apparent from theory and experience that 20% sulfation of PPS is not theoretically possible unless the sodium is substituted with hydrogen giving pentosan hydrogen sulfate (in which case maximum sulfation is 21.9%). The highest possible degree of sulfation for physiologically active PPS is 18.9 to 19%, depending on the length of the molecule. Indeed to date, there is also no substantiation in the prior art of 19% sulfation for PPS, let alone higher degrees of sulfation.

Differences in the manufacturing process (especially during hydrolysis and sulfation) can result with molecular differences of the PPS molecule, such as the degree of sulfation and the position of sulfate groups on the glycan chain. It is well known that the clinical efficacy of sulfated carbohydrates can be affected by the type and position of $SO_3^-$ groups, hence the need to fully control and characterise molecules. This is well known in relation to heparin but to date this knowledge has not been adequately applied to the PPS molecule(s).

Prior art NMR analyses of sulfate esters (such as U.S. Pat. No. 4,713,373) use NMR peak ratios to calculate degrees of sulfation. However, NMR peak ratios will not necessarily indicate the degree of sulfation of the molecule unless the calculation is made by analysis of the entire NMR spectrum.

The PPS prior art fails to characterise the position of $SO_3^-$ groups (other than to describe theoretical full sulfation) or to discuss the molecular subspecies. There has been no disclosure in the prior art of where the sulfur is missing along the glycosaminoglycan or glycan chain when there is less than full sulfation. The prior art acknowledges that PPS mixtures differ but focus only on the level of sulfation and average molecular weight as being factors that may significantly affect physiological efficacy of the PPS material.

Studies with heparin show the efficacy of varying molecular species (of heparin) depends on the location of the $—OSO_3$ groups within the molecule. Specifically, the relationship of chemical structure to activity for heparin is isolated to a pentasaccharide sequence comprising three D-glucosamine and two uronic acid units. The central D-glucosamine unit in this sequence contains a 3-O-sulfate moiety that is rare outside of this sequence. Sulfate groups on the D-glucosamines are found to be critical for retaining high anticoagulant activity, while undersulfation at less important locations seems not to affect the anticoagulant activity.

Different manufacturing techniques lead to different types (chemical structures) of heparin being produced and these different structures are shown to have different clinical efficacies. By way of analogy, the molecular species of other glycan chains (including PPS) vary according not only to the degree of sulfation but also according to the location of the sulfur atoms. The PPS prior art does not address this in any detail.

While use of PPS became widespread, and to reduce batch to batch variations that could affect pharmaceutical effectiveness, the fundamental problem to overcome was production of a PPS molecular species with a constant sulfur content close to or at 18 to 19%, with narrow average molecular weight range that ensures consistent physiological benefits and sulfate groups consistently attached to positions that will guarantee physiological effect. To date, there has been no discussion in the prior art regarding the relative importance of the positions of the sulfate groups on the glycosaminoglycan or glycan chain.

Broad Spectrum Molecular Weight

PPS is derived from natural sources such as beechwood xylan. In its natural form, PPS consists of molecular chains of varying lengths, or molecular weights. However, like heparin, the effects of unfractionated natural PPS can be difficult to predict.

Clinical experience with heparin has found that by modifying heparin and making the mixture of molecules more homogenous (with a narrower molecular weight range), greater clinical efficacy, consistency and safety can be achieved. Similar experience has emerged in the clinical use of PPS.

However, in practice, it has been difficult to achieve consistency of the heterogeneous mixture of carbohydrates that make up PPS during commercial production. This is because it has been difficult to achieve a consistent average molecular weight, consistently low molecular weight and steady but high level of sulfation.

OBJECT OF THE INVENTION

It is an object of the present invention to overcome or ameliorate at least one of the disadvantages of the prior art, or to provide a useful alternative.

According to one aspect of the invention there is provided a sulfated glycan (sulfate ester) molecule having:
(a) one or more linear 1-4 conjugated beta-D-xylose units; and
(b) at least one 4-O-methyl-β-D-glucuronic acid unit attached to carbon-2 of every about eight to ten (on average) said xylose units.

According to another aspect of the invention there is provided a sulfated glycan (sulfate ester) molecule having:
(a) one or more linear 1-4 conjugated beta-D-xylose units; and
(b) at least one 4-O-methyl-β-D-glucuronic acid unit attached to carbon-2 of every about eight to ten (on average) said xylose units,
wherein said molecule has the following configuration of $SO_3^-$ groups when Fully Sulfated:
  (i) two $SO_3^-$ groups on each said glucuronic acid unit(s), regardless of the position of said glucuronic acid unit(s) along said molecule;
  (ii) three $SO_3^-$ groups on a terminal xylose unit when said xylose unit is not holding a glucuronic acid group;
  (iii) two $SO_3^-$ groups on a terminal xylose unit when said xylose unit is holding a glucuronic acid group;
  (iv) two $SO_3^-$ groups on a mid-chain xylose unit when said mid-chain xylose unit is not holding a glucuronic acid group;
  (v) one $SO_3^-$ group on a mid-chain xylose unit when said mid-chain xylose unit is holding a glucuronic acid group.

According to yet another aspect of the invention there is provided a sulfated glycan (sulfate ester) molecule having:
(a) one or more linear 1-4 conjugated beta-D-xylose units; and
(b) at least one 4-O-methyl-β-D-glucuronic acid unit attached to carbon-2 of every about eight to ten (on average) said xylose units,
wherein said molecule has the following preferential configuration of $NaSO_3^-$ groups when Highly Sulfated:
  (i) up to two $SO_3^-$ groups on each said glucuronic acid unit(s), regardless of the position of said glucuronic acid unit(s) along said molecule;
  (ii) up to three $SO_3^-$ groups on a terminal xylose unit when said xylose unit is not holding a glucuronic acid group;
  (iii) up to two $SO_3^-$ groups on a terminal xylose unit when said xylose unit is holding a glucuronic acid group;
  (iv) up to two $SO_3^-$ groups on a mid-chain xylose unit when said mid-chain xylose unit is not holding a glucuronic acid group; and
  (v) up to one $SO_3^-$ group on a mid-chain xylose unit when said mid-chain xylose unit is holding a glucuronic acid group,
such that no more than a total of two $SO_3^-$ groups is absent from a Fully Sulfated State.

According to a further aspect of the invention there is provided a mixture comprising sulfated glycan (sulfate ester) molecules wherein said molecules have the following typical chemical structure:
(a) one or more linear 1-4 conjugated beta-D-xylose units; and
(b) at least one 4-O-methyl-β-D-glucuronic acid unit attached to carbon-2 of every about eight to ten (on average) said xylose units.

According to yet a further aspect of the invention there is provided a mixture comprising sulfated glycan (sulfate ester) molecules wherein said molecules have the following typical chemical structure:
(a) one or more linear 1-4 conjugated beta-D-xylose units; and
(b) at least one 4-O-methyl-β-D-glucuronic acid unit attached to carbon-2 of every about eight to ten (on average) said xylose units,
wherein said glucuronic acid unit preferentially resides on a left terminal xylose unit.

According to still a further aspect of the invention there is provided a mixture comprising sulfated glycan (sulfate ester) molecules wherein said molecules have the following typical chemical structure:
(a) one or more linear 1-4 conjugated beta-D-xylose units; and
(b) at least one 4-O-methyl-β-D-glucuronic acid unit attached to carbon-2 of every about eight to ten (on average) said xylose units,
wherein said glucuronic acid unit preferentially resides on a right terminal xylose unit.

According to yet another aspect of the invention there is provided a mixture comprising sulfated glycan (sulfate ester) molecules wherein said molecules have the following typical chemical structure:
(a) one or more linear 1-4 conjugated beta-D-xylose units; and
(b) at least one 4-O-methyl-β-D-glucuronic acid unit attached to carbon-2 of every about eight to ten (on average) said xylose units,
wherein said glucuronic acid unit preferentially resides on a mid-chain xylose unit.

According to yet a further aspect of the invention there is provided a method for the production of a mixture comprising sulfated glycan molecules wherein said molecules comprise:
(a) one or more linear 1-4 conjugated beta-D-xylose units; and
(b) at least one 4-O-methyl-β-D-glucuronic acid unit attached to carbon-2 of every about eight to ten (on average) said xylose units.

According to a further aspect of the invention still there is provided a method for fractionation of sulfated glycan (sulfate ester) molecules derived from xylan using an organic solvent.

According to still another aspect of the invention there is provided a method for purification of a mixture comprising sulfated glycan (sulfate ester) molecules, wherein said purification involves fractionation using an organic solvent.

According to yet another aspect of the invention there is provided a method for decolouration of a mixture comprising sulfated glycan (sulfate ester) molecules, wherein said decolouration involves:
(a) charcoal;
(b) chlorine;
(c) peroxide;
(d) fractionation using an organic solvent; or
(e) any combination of the above.

According to yet a further aspect of the invention there is provided a therapeutic formulation of sulfated glycan (sulfate ester) molecules suitable for parenteral administration wherein said formulation includes sulfated glycan (sulfate ester) molecules in aqueous solution.

According to a further aspect of the invention yet there is provided a therapeutic formulation of sulfated glycan (sulfate ester) molecules suitable for oral administration.

According to yet another aspect of the invention there is provided a delivery mechanism for the administration of a therapeutic formulation of sulfated glycan (sulfate ester) molecules, wherein said delivery mechanism is a pen-like delivery device that enables:
(a) dial-up dosing;
(b) pre-loading with a unit-dose cartridge;
(c) a combination of the above.

According to yet a further aspect of the invention there is provided a mixture of sulfated glycan (sulfate ester) molecules suitable for use as an antioxidant.

According to another further aspect of the invention there is provided an antioxidant comprising sulfated glycan (sulfate ester) molecules.

BRIEF DESCRIPTION OF THE DRAWINGS

A preferred embodiment of the invention will now be described, by way of example only, with reference to the accompanying drawings in which:

FIG. 10 is a table containing exemplary data obtained from size exclusion chromatography of unfractionated GXS and fractionated GXS (obtained at the ethanol concentrations listed).

DETAILED DESCRIPTION

A preferred embodiment of the present invention will now be described by reference to the drawings. The following detailed description in conjunction with the figures provides the skilled addressee with an understanding of the invention. It will be appreciated, however, that the invention is not limited to the applications described below.

Dictionary of Defined Terms

Table 1 is a dictionary of terms defined according to the invention. Terms defined in Table 1 are denoted with the use of capitalisation throughout the document. If a term is not capitalised then its plain meaning is to be construed, unless otherwise specified.

TABLE 1

Dictionary of defined terms

| Term | Description |
|---|---|
| Degree of Sulfation | Measurement of the relative composition of sulfur in a glycan molecule. This is measured as relative molecular weight of the sulfur expressed as a percentage of the molecular weight of the whole chain. See below for "full", "high" and "partial" sulfation definitions. |
| Full Sulfation, Fully Sulfated, Fully Sulfated State | Saturation of a glycan molecule in which sulfur occupies all available positions on the xylose units and glucuronic acid units in the glycan chain. Full sulfation of the glycan chain is 18.9% (when sodium is not substituted with hydrogen, as discussed in problems of the prior art). |
| GXS | Glucuronoxylan sulfate anion and its salts |
| PPS | Pentosan polysulfate sodium |
| High Sulfation, Highly Sulfated, Highly Sulfated State | High sulfation of the glycan chain is 18% or greater sulfation. |
| Mp | Molecular weight at the top of a size exclusion chromatography peak |
| Partial Sulfation, Partially Sulfated, Partially Sulfated State | Partial sulfation is less than 18% sulfation. In practice, prior art PPS molecules (which are a glycan chain) have not exceeded 17% sulfation unless sodium is substituted with hydrogen, resulting in pentosan hydrogen sulfate rather than PPS. |
| Selective fractionation | In this document selective fractionation means fractionation with an organic solvent such as ethanol performed in an alkaline (e.g. pH 9.0) solution |

The elements of the invention are now described under the following headings:

A Preferred Embodiment of a Sulfated Polysaccharide Compound: GXS

The present invention provides a novel sulfated glycan (sulfate ester) molecule. The new molecule is the first known molecule to achieve high and full sulfation of the xylan chain and shall be referred to as glucuronoxylan sulfate (GXS). GXS is distinct from known PPS molecules, as shown by chemical analysis and clinical performance studies (as discussed later in this document). No method currently disclosed in the prior art is able to achieve high or full sulfation of the PPS molecule.

Chemical Structure

According to the prior art, PPS consists of sulfated linear 1-4 conjugated beta-D-xylopyranose units and has 4-O-methyl-β-D-glucuronic acid randomly attached at carbon-2 on every eight to ten xylose units (on average).

Figure 1:
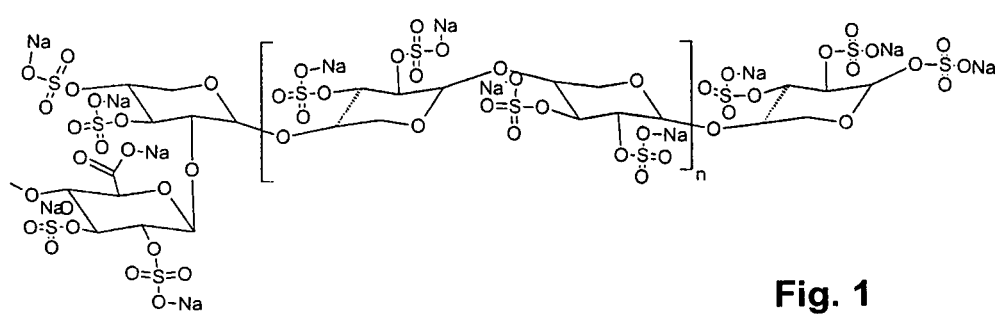
FIG. 1 is a diagrammatic representation of a preferred embodiment of GXS showing the points of sulfation on xylose units making up the glycan chain and the presence of a glucuronic acid unit on the left terminal xylose unit.

One arrangement of the preferred embodiment is a mixture of GXS molecules in which at least 10% of molecules in the mixture are Fully Sulfated. The term "full sulfation" is used by the applicant to refer to a configuration of the GXS molecule as illustrated in FIG. 1, with the following composition of $SO_3^-$ groups:

(a) on the right terminal xylose unit illustrated, there are three $SO_3^-$ groups;
(b) on each mid-chain xylose unit, there are two $SO_3^-$ groups; and
(c) on the left terminal xylose unit, there is a glucuronic acid unit (defined by a carboxyl unit and an —$OCH_3$ [4-methoxy] group) and two $SO_3^-$ units.

The above configuration is based on the scientific literature (e.g. Friedrich Cavagna, Hans Deger, Jurgen Puls, *Carbohydrate Research* 129 (1984) 1-8), which indicates that 97% of molecules in a mixture of hydrolysed glycan isomers will have the glucuronic acid unit on the left terminal pentose. It is also well known that carboxyl groups in molecular species such as enzymes often indirectly participate and guide/catalyse hydrolysis. Furthermore, 3D modelling software (specifically, proprietary software known as ACD/3D Viewer by Advanced Chemistry Development, Inc.) indicate that in the non-hydrolysed sulfated xylan macromolecule, xylose units derivatised with glucuronic acid will be in twisted-boat conformation, adding conformational and steric reasons to the directed hydrolysis (guided by glucuronic acid). This is in contrast to the PPS prior art that claims random allocation of glucuronic acid units on the left, right and mid-chain xylose units.

The preferred embodiments enable a high yield of highly and/or fully sulfated glycans. The isomers of these glycans can be separated using electrophoresis, chromatography or similar techniques, thereby producing compounds with potentially greater pharmaceutical or therapeutic efficacy.

In a first preferred embodiment, the GXS is fractionated using an organic solvent. No known PPS molecules extracted from xylan are fractionated in this way. In a second preferred embodiment, the GXS is unfractionated. All comments in the detailed description apply to all embodiments and arrangements of the invention, unless specifically stated otherwise.

In all arrangements, the preferred embodiment is a semi-synthetic GXS with 18% or greater sulfation, as verified by testing for degree of sulfation (expressed as a weight percentage of the composition of the glycan chain). Table 1 contains examples of testing from three batches, demonstrating greater than 18% sulfation of GXS synthesised as a sodium salt using the inventive method:

TABLE 1

Degree of sulfation

| | % sulfation |
|---|---|
| Batch 1 | 18.2 |
| Batch 2 | 18.0 |
| Batch 3 | 18.4 |

GXS is an anion and may exist in a wide array of practical embodiments, by attaching to various counter ions such as inorganic metals (e.g. Na, K, Ca, Mg, Ag) or organic bases. Further examples are also included in the section "1.2 Conversion of the pyridinium salt to a sodium salt, as an exemplary arrangement of the preferred embodiment".

The degree of sulfation of the preferred embodiment is distinguished from known glycan chains derived from xylan (described in the prior art as PPS molecules), which have less than 17% sulfation in practice. The applicant suggests this is due to a novel difference in the method of preparation of GXS compared with known PPS, as described later in this document.

The degree of sulfation of GXS compared with PPS has been ascertained through proton nuclear magnetic resonance (NMR) spectrometry, conducted by an independent laboratory using the same methodology (50 mg/mL $D_2O$ with or without trifluoroacetic acid) and equipment (600 MHz) across samples of three different glycan compounds, each derived from xylan but manufactured by a different source. The three different compounds analysed were as follows:

(a) compound A (see FIG. 2)—a PPS compound;
(b) compound B (see FIG. 3)—a PPS compound; and
(c) the inventive compound (compound C—see FIG. 4)—a GXS compound.

Figure 2:
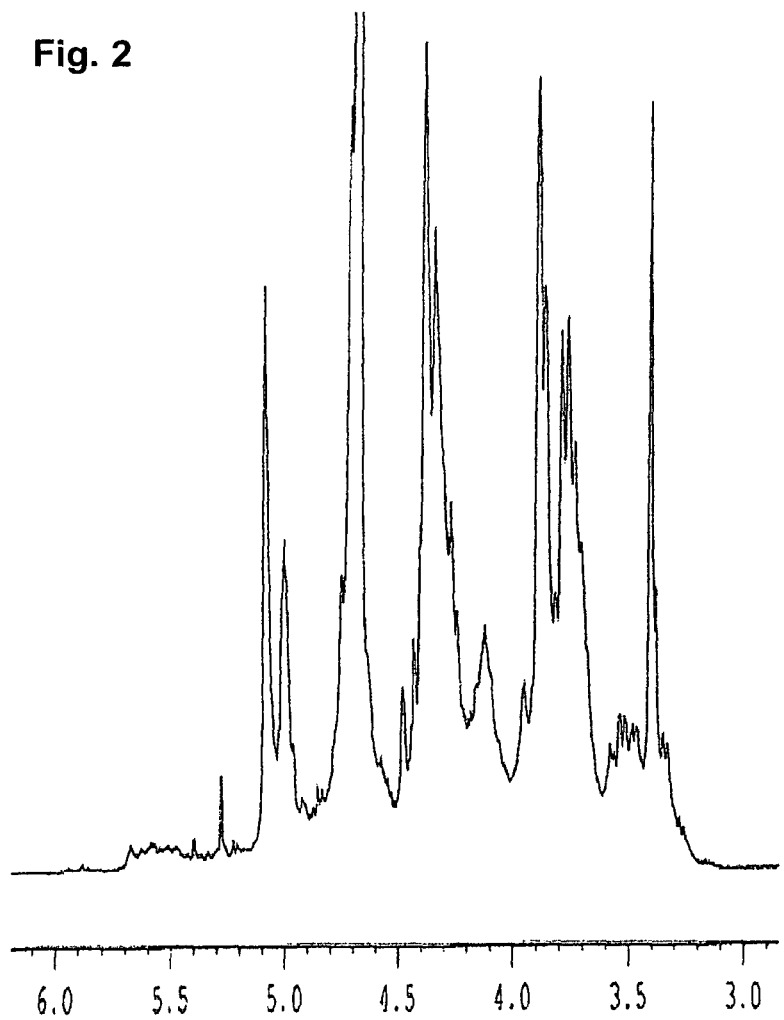
FIG. 2 is an example of a typical result from NMR spectrometry of prior art PPS compound A.
Figure 3:
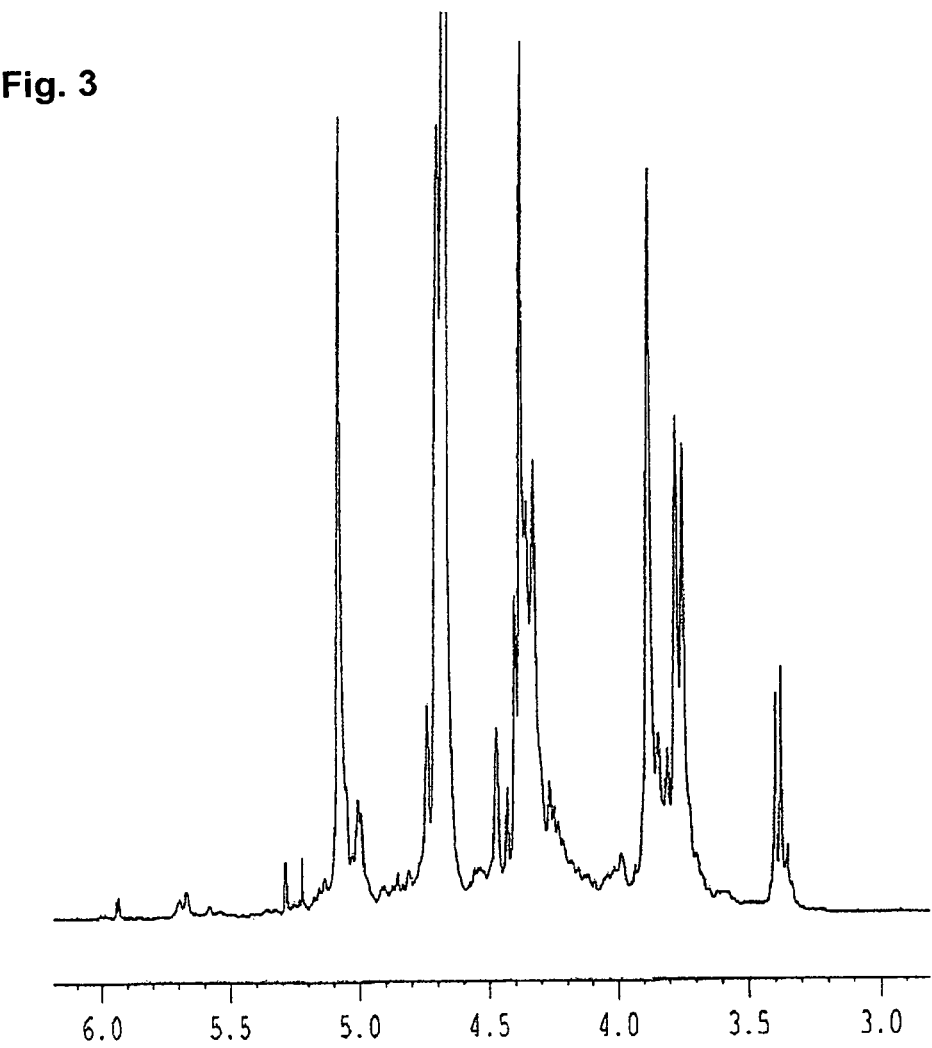
FIG. 3 is an example of a typical result from NMR spectrometry of prior art PPS compound B.
Figure 4:
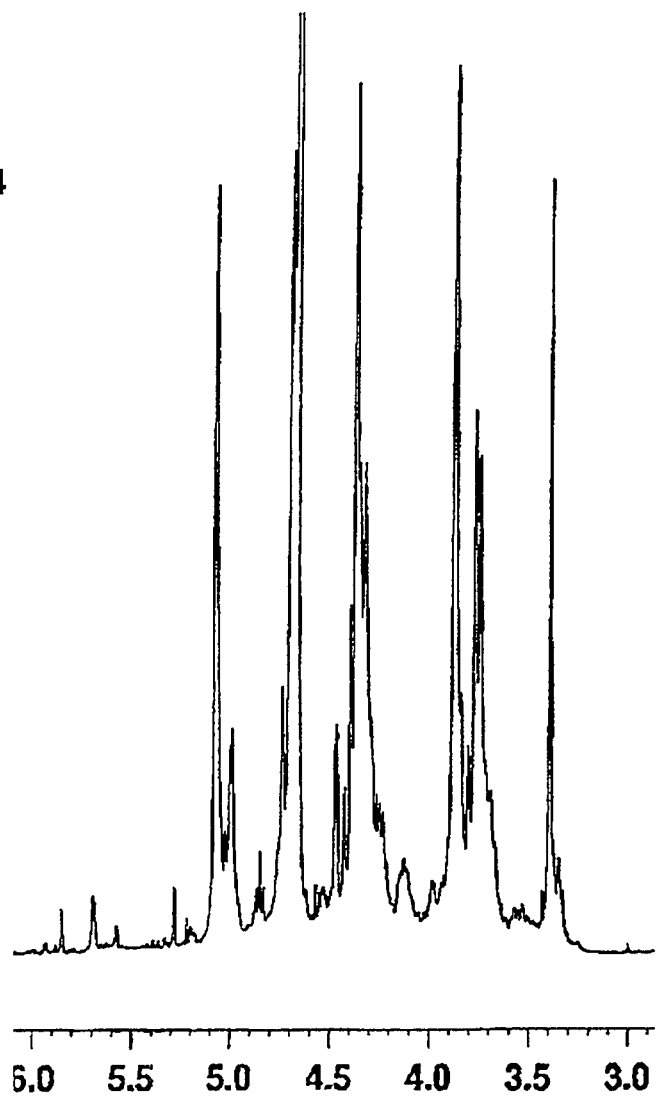
FIG. 4 is an example of a typical result from NMR spectrometry of the preferred embodiment, compound C.

Examples of the NMR analyses of the different compounds are demonstrated in FIGS. 2 to 4. The inventive compound, compound C, differs from the prior art PPS compounds, as indicated by the NMR analyses (and other analyses described below). The exact NMR peak shifts will differ according to experimental conditions such as temperature, concentration of sample, solvent used, and so on. Therefore, all NMR peak shifts are approximate and indicative only.

Referring to FIG. 2, the intensity of the peak seen at 5.1 ppm indicates incomplete sulfation of compound A at position 2 of the xylose subunits. To clarify, the peak at 5.1 ppm is due to the NMR shift of protons at C1 of the xylose units when a sulfate group is present at C2 (meaning that the shift of that C1 proton will not be at 5.1 ppm if there is no sulfation at C2). Therefore, the peak at 5.1 ppm is an indirect measure of sulfation at position 2 of the xylose units.

The peak at approximately 3.4 ppm is due to the OCH3 group of glucuronic acid. The presence of a strong single peak at approximately 3.4 ppm indicates consistent sulfation at both positions 2- and 3- of the glucuronic acid unit in compound A.

Referring now to FIG. 3, the intensity and appearance of two peaks at 3.4 ppm indicate inconsistent sulfation of compound B at positions 2- and 3- of the glucuronic acid unit. Furthermore, NMR prediction software indicated that fully sulfated glucuronic acid units will be presented with peak at about 5.3 ppm, while presence of peak at 5.2 ppm is typical for partially sulfated glucuronic acid ($SO_3$ group missing at position 3). Therefore, presence of two peaks at approximately 3.4 and another two peaks at 5.2-5.3 ppm region indicated inconsistent sulfation of glucuronic acid of compound B.

Comparing both FIGS. 2 and 3, the NMR spectra of both compounds A and B are showing no significant traces of peaks at 5.85 ppm and 5.7 ppm. According to theoretical calculations and experimental chemical structure database searches conducted by NMR modelling and prediction software (specifically, proprietary software known as ACD/C+H NMR Predictors and DB by Advanced Chemistry Development, Inc.):

(a) the 5.85 ppm peak will be related to a fully sulfated right terminal xylose (with three sulfate groups); and
(b) the 5.7 ppm peak indicates that two (probably at positions 1 and 3) out of three possible sulfate groups at right terminal xylose will be present.

Therefore, peaks at 5.85 ppm and 5.7 ppm indicate a mixture of fully and partially sulfated molecules (at the right terminal xylose). Since both of these peaks are virtually negligible for compound A and compound B, this indicates that neither compound has achieved full theoretical sulfation.

FIG. 4 contains an example of NMR spectrometry data from GXS. The NMR in FIG. 4 demonstrates the significant presence of fully sulfated molecules and the existence of sulfate ($SO_3^-$) groups at all xylose units along the newly created glycan chain known as GXS.

Figure 5:
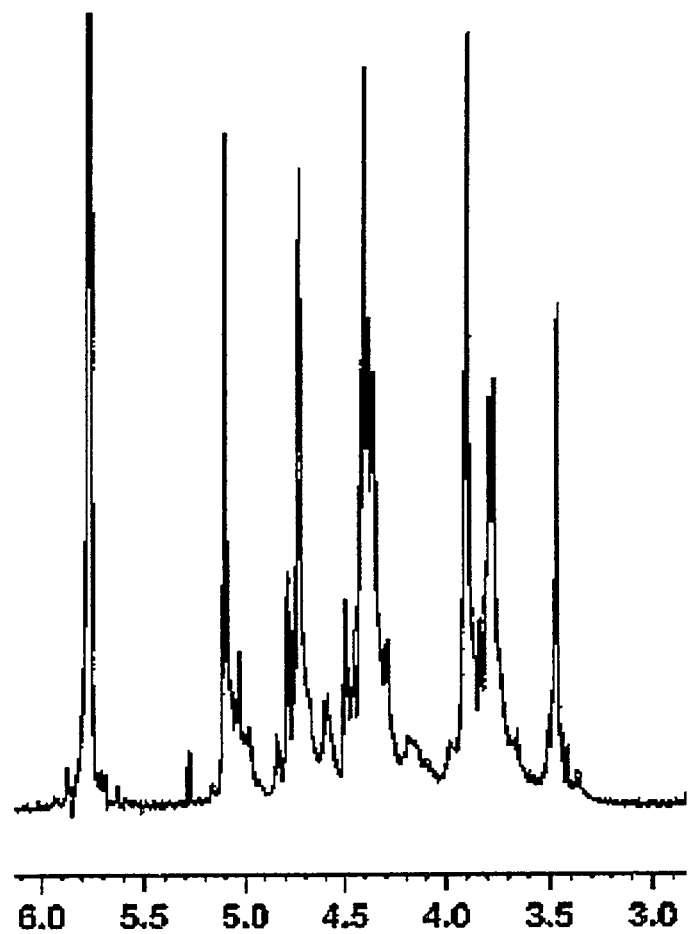
FIG. 5 is an example of a typical result from NMR spectrometry of the preferred embodiment, compound C, but with the addition of trifluoroacetic acid to the $D_2O$ solution of GXS, in order to move the water peak that partially obscures the peak at 4.7 ppm.

Specifically, full sulfation of all xylose units in GXS is indicated by the appearance of peaks at 5.1 ppm, 4.7 ppm (see also FIG. 5), 4.4 ppm and 3.8 ppm as shown in FIG. 4. The NMR peak at 4.7 ppm is more clearly seen in FIG. 5, which has been collected by the addition of trifluoroacetic acid to the $D_2O$ solution of GXS, in order to move the water peak (visible in FIG. 4 at around 4.7 ppm) and shows full sulfation of that peak. The other peaks can be seen fully in FIG. 4. The addition of TFA is not the preferred mode of NMR spectra collection as the addition of such a strong acid could affect the appearance of some small yet important peaks or even induce a small change of GXS structure which is susceptible to acid degradation.

The strong single NMR peak at approximately 3.4 ppm indicates consistent sulfation and the 5.3 ppm peak indicates full sulfation of glucuronic acid. Additionally, the peaks at approximately 5.85 ppm and 5.7 ppm indicate a mixture of a fully sulfated right terminal xylose unit and a partially sulfated right terminal xylose unit (with $SO_3$ groups at positions 1 and 3). Therefore, predictive modelling of the NMR data indicated that the inventive compound GXS is a mixture of fully sulfated and highly sulfated molecules, with large number of fully sulfated molecules.

Figure 6:
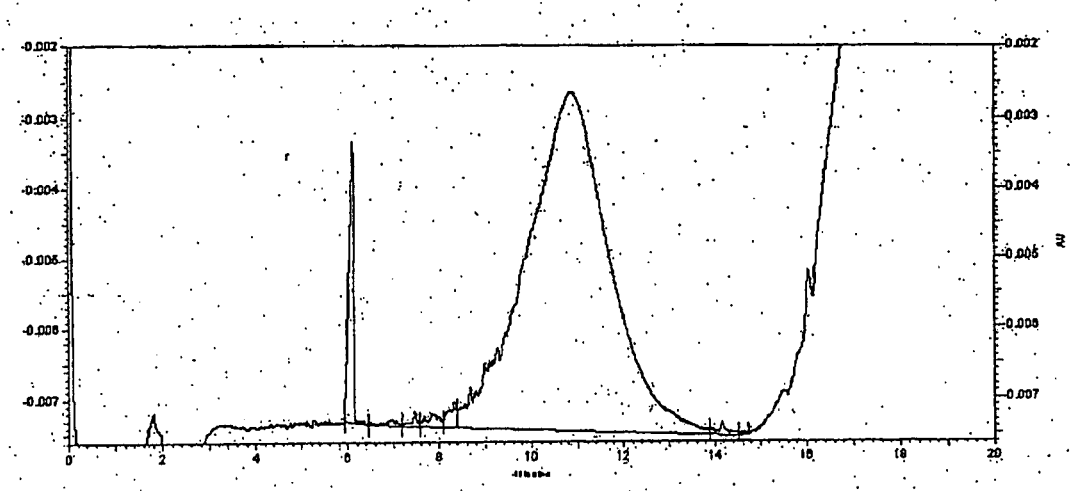
FIG. 6 is an example of a typical capillary zone electrophoresis profile of PPS compound A.
Figure 7:
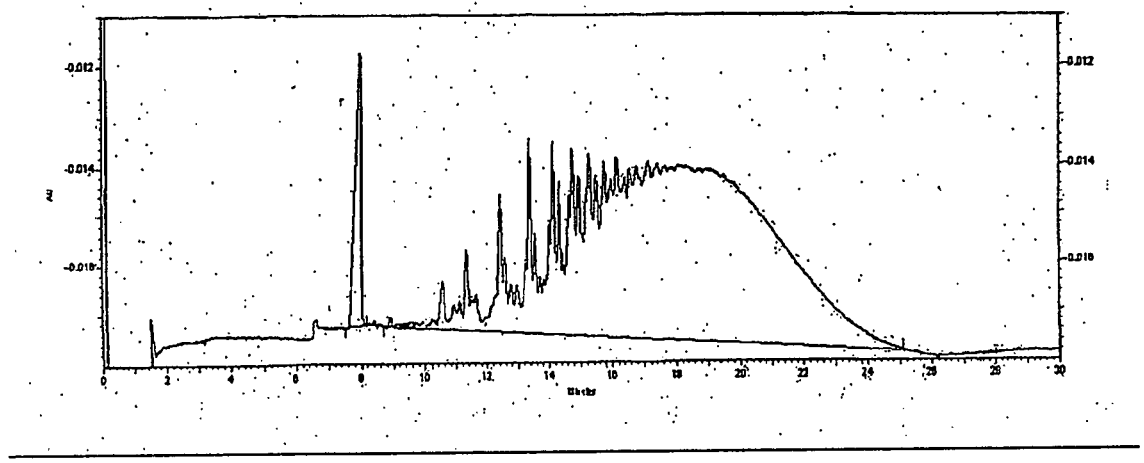
FIG. 7 is an example of a typical capillary zone electrophoresis profile of PPS compound B.

FIGS. 6 and 7 contain typical sample capillary zone electrophoresis (CZE) profiles of compounds A (FIG. 6) and B (FIG. 7), respectively. Compound B is the pioneer PPS compound released onto the market for use in osteoarthritis. The manufacturer of compound A (Manufacturer A) subsequently released a compound (A) with the bell-shaped CZE profile shown in FIG. 6 as a type of PPS. Manufacturer B previously used the difference in CZE profiles (namely, the shorter oligosaccharide peaks in the CZE profile of compound A compared with compound B) to argue that the bell-shaped PPS is not a generic copy of the PPS molecule that is compound B.

Manufacturer A is the applicant of patent application no. WO 2007/123800, in which it disputes the importance of well defined CZE peaks (short oligosaccharides). The bell-shaped curve component of the CZE profile represents a large number of molecular species. By contrast, well-defined peaks in a CZE profile represents a smaller number of molecular species—in FIG. 7, the peaks occur on the left of the bell-shaped curve, indicating a lower number of molecular species in the lower molecular weight range. The bell-shaped curve for Manufacturer A's compound has a sharper profile than that of compound B (seen by comparing FIGS. 6 and 7). Manufacturer A has used this to support an inference that the area under the curve represents a greater number of low molecular weight species.

Figure 8:
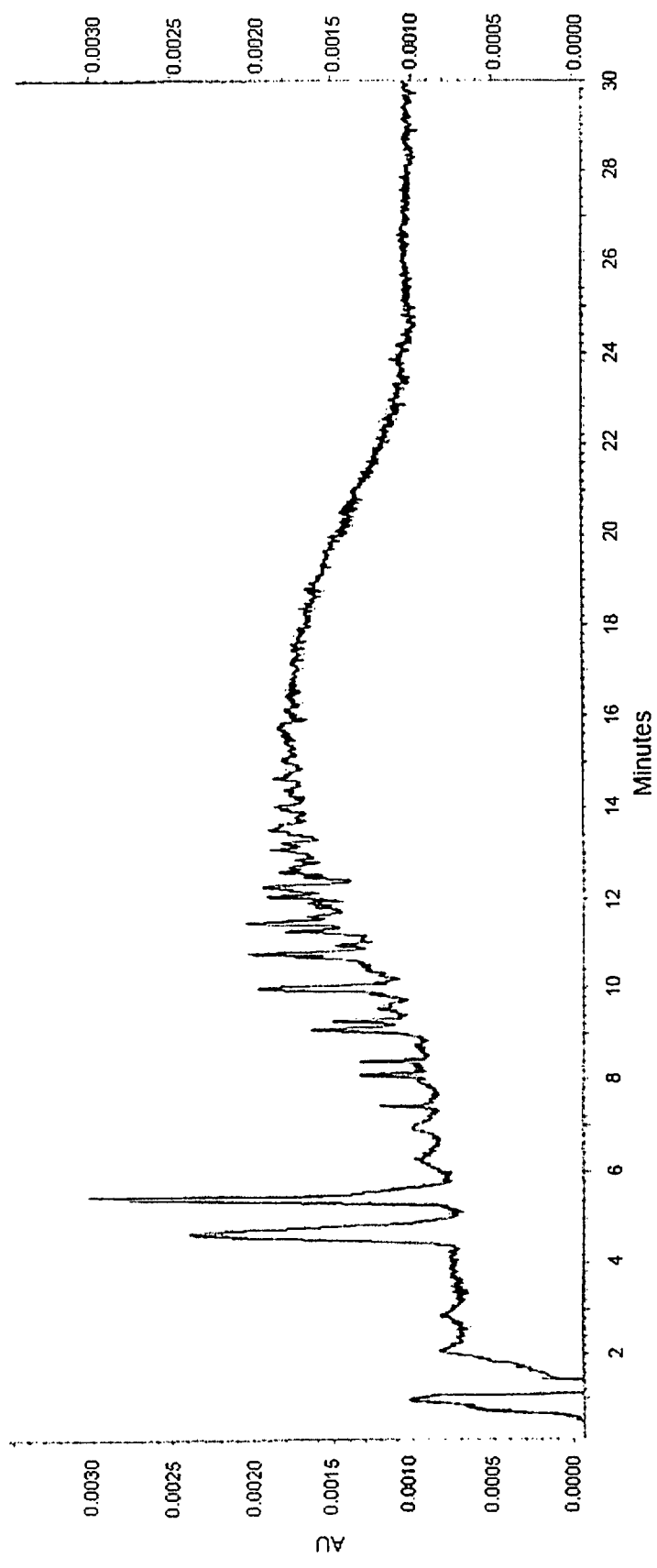
FIG. 8 is an example of a typical capillary zone electrophoresis profile of the preferred embodiment, compound C.

A typical CZE profile of the unfractionated preferred embodiment is contained in FIG. 8. The profile contains a large number of well-defined peaks (short oligosaccharides) to the left, continuing into the bell-shaped curve. One interpretation of the CZE profile is that it indicates that the incidence of molecular species in the lowest molecular weight range for Compound C (GXS) is greater than for compounds A and B.

Although the CZE profiles of GXS (Compound C) and Compound B PPS have similarities, the NMR profiles of the two compounds unequivocally show very important differences in chemical structure between the two molecules. NMR is a better technique for distinguishing molecular structure of glycans than CZE and NMR is widely recognised as a premier chemical signature technique. CZE cannot be relied on with the same accuracy for determining the chemical signature of a molecule.

A Method of Preparing GXS from Xylan: a Preferred Embodiment

A preferred embodiment provides a novel method for production of xylan sulfates (specifically, the GXS described above) from beechwood xylan. The production method includes the steps of:

(a) performing a novel double sulfation technique using pyridine chlorosulfonic acid complex in DMF, pyridine $SO_3$ complex in DMF or a combination of these in solvent;
(b) ultrafiltration to remove inorganic impurities (e.g. divalent cations) and some of very low MW degradation products from the GXS. Ultrafiltration can occur at one or more stages throughout the production method; and
(c) in relation to the fractionated GXS embodiment, performing fractionation with an organic solvent such as ethanol, to produce narrow distribution low MW GXS molecules and as a novel means for decolouration. No known method for extracting prior art PPS molecules from xylan involves a fractionation step using an organic solvent or a mixture including an organic solvent. Further, the applicant's fractionation method includes the novel steps of:
  i. selective fractionation of the GXS mixture (obtained from the double sulfation method) using an organic solvent, to increase the yield of highly and fully sulfated GXS molecules;
  ii. modification of the pH of the molecule/solvent solution to make it alkaline (thereby selectively precipitating out the higher MW molecules); and
  iii. use of selective fractionation as a means to remove colour (a colour change from one fraction to the next indicates chemical degradation which results in colouration of the precipitate).

1. Sulfation Principle 1.1 Production of Xylan Polysulfate Pyridine Salt

Xylan reacts under certain conditions with pyridine chlorosulfonic acid, pyridine $SO_3$ or a combination to form sulfated xylan esters. The reaction medium contains a proton acceptor (N,N-dimethyl formamide (DMF)), which may be a higher polar aprotic solvent. The equations include:

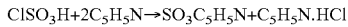

$ClSO_3H + 2C_5H_5N \rightarrow SO_3C_5H_5N + C_5H_5N.HCl$

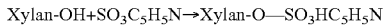

$Xylan\text{-}OH + SO_3C_5H_5N \rightarrow Xylan\text{-}O\text{---}SO_3HC_5H_5N$

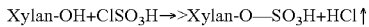

$Xylan\text{-}OH + ClSO_3H \rightarrow Xylan\text{-}O\text{---}SO_3H + HCl\uparrow$ In the presence of DMF, quantitative reaction of pyridine with chlorosulfonic acid, for example, immediately yields $SO_3HC_5H_5N$ and a mole of pyridinium chloride. The $SO_3HC_5H_5N$ reacts with xylan to form xylan-O—$SO_3HC_5H_5N$, which has good solubility in DMF. The highly polar DMF associates with the hydroxyl groups of the substrate and makes them more accessible to the $SO_3$-pyridine complex, which is utilised as a sulfate donor. The use of excess pyridine and DMF and lower sulfation temperature can not only avoid degradation but forms a homogenous system, which results in a more complete reaction.

The hydrogen chloride formed in the reaction mixture can be absorbed in water through a $CaCl_2$ tube. The temperature (75° C.) keeps the xylan dissolved in the reaction system and gives a higher degree of sulfation. The pyridinium salt of sulfated xylan is recovered and purified by methanol precipitation.

1.2. Conversion of the Pyridinium Salt to a Sodium Salt, as an Exemplary Arrangement of the Preferred Embodiment The pyridinium salt can be converted to the sodium salt by raising the pH to a level where the pyridine is not protonated, and is released as free pyridine. This reaction is reversible.

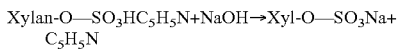

$Xylan\text{-}O\text{---}SO_3HC_5H_5N + NaOH \rightarrow Xyl\text{-}O\text{---}SO_3Na + C_5H_5N$ High pH accelerates the conversion to the sodium salt, but it can cause degradation. A pH of 9.5-10 is suitable. The free residual pyridine and DMF are removed by rotary evaporation at 50° C.

In alternative arrangements, the pyridinium salt can be converted to other salts, by attaching to any other suitable counter ion such as an inorganic metal (e.g. Na, K, Ca, Mg, Ag) or an organic base. Suitable examples include:

(i) Glycine ethyl ester (or other amino acid ester)
(ii) Glucosamine
(iii) Procaine
(iv) Tetracaine
(v) Triethanolamine (used as triethanolamine salicylate)
(vi) Benzathine
(vii) Choline (used as choline salicylate)
(viii) Benorylate
(ix) Imipramine
(x) Penicillamine
(xi) Trimethoprim
(xii) Mesalamine
(xiii) Meglumine (N-methyl glucamine)
(xiv) 4-methyl2-hexanamine(methylhexaneamine)
(xv) p-amino hippuric acid.
(xvi) 2-amino-2-methyl-1,3-propanediol
(xvii) 2-amino-4-picoline
(xviii) 4-amino salicylic acid
(xix) Pyrilamine
(xx) Guanine.

1.3. Control of Molecular Size and Decolouring

Xylan from a commercial source (e.g. Sigma or Kaden) has a larger molecular weight (10,000 to 50,000) than required. Theoretically, complete sulfation will make the molecular weight (MW) of the final sulfated xylan increase to 2.5 times that of the starting xylan. To ensure a final MW of approximately 1000 to 6000, three methods can be used:

I. xylan is directly sulfated following hydrolysis to suitable molecular size;
  II. the reduction of molecular size and decolouring can be carried out simultaneously by carrying out the reaction in acidic medium containing hydrogen peroxide or chlorine; or
  III. xylan is directly sulfated, acid hydrolysed to a suitable molecular size, and the resulting product is resulfated.

Methods (II) and (III) have been shown to be efficient methods to obtain a sulfated low molecular weight, low viscosity GXS. The sulfated product is very water-soluble compared to native xylan so subsequent depolymerisation and dialysis are easier to perform. However, both methods (I) and (II) have disadvantages.

In method (II), although sulfation followed by depolymerisation is a convenient way to obtain the desired molecular size, acid hydrolysis at high temperature (80-100° C.) also causes some desulfation. As a result, the NMR spectrum of the final product is unsatisfactory. There is also a problem with residual oxidative power imparted by the hydrogen peroxide, so it is strongly recommended that chlorine be used.

In method (I), although depolymerisation followed by sulfation yields a satisfactory sulfation content, the depolymerisation step gives poor yields owing to the low solubility of the native polymer in acid, leading to a heterogeneous reaction difficult to reproduce. In addition, it is not easy to desalt depolymerised, unsulfated xylan by dialysis because of low solubility leading to membrane blockage.

It is also known that exposure of sulfated xylan to extreme conditions such as acidic environment and heat during hydrolysis could lead to the loss of sulfur and opening of new positions for potential sulfation.

The disadvantages of methods (I) and (II) may be overcome by sulfation followed by depolymerisation, then resulfation method (III). Introducing sulfate groups greatly improves the solubility of xylan, and the depolymerisation step gives higher yields. Desulfation during hydrolysis can be overcome by resulfation. Though this method is more costly of reagents and is time consuming, it has been adopted by the applicant.

2. Double Sulfation Method to Produce Unfractionated but Highly Sulfated GXS: A Preferred Embodiment Methods of production of known sulfate esters (PPS) from xylan involve sulfation then acid hydrolysis. During the hydrolysis step, there is a loss of sulfur and new OH groups are opened up available for sulfation. In this way, acid hydrolysis results in a reduction in the degree of sulfation of the end product. Known methods do not address this disadvantage. The double sulfation method of the preferred embodiment introduces a second sulfation stage after acid hydrolysis to replenish sulfur lost during hydrolysis. This is described below.

2.1. Sulfation of Xylan

Figure 9:
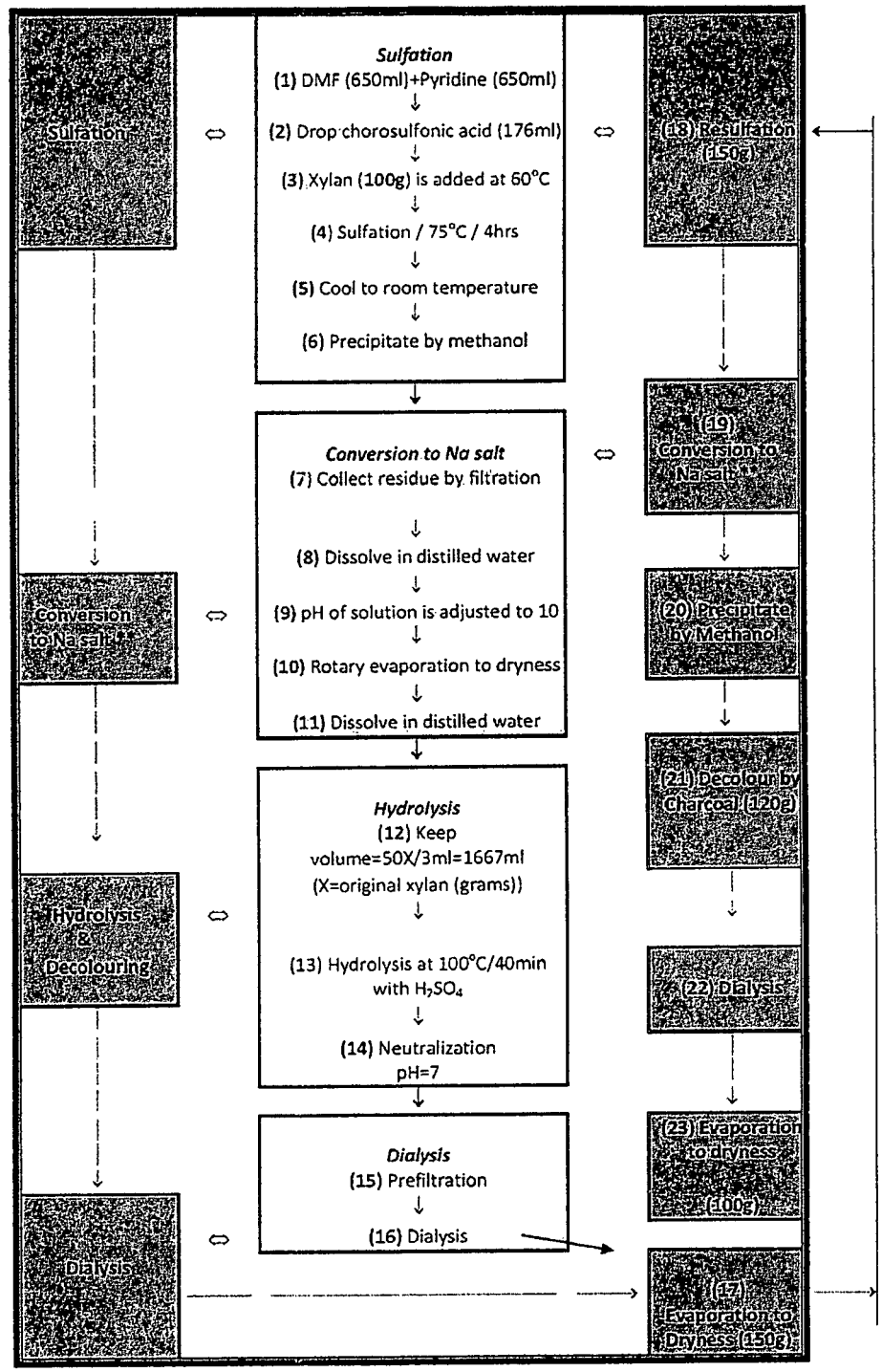
FIG. 9 is a flowchart outlining a preferred embodiment of the double sulfation method.

Referring to step 1 in FIG. 9, a mixture of equal volumes of anhydrous pyridine and anhydrous DMF is mechanically stirred for half an hour at approximately 0° C. in an ice bath. For example, a mixture of 650 mL anhydrous pyridine and 650 mL anhydrous DMF is added into a 5 L two necked round-bottom flask provided with a mechanical stirrer, a thermometer (0-100° C.) and a 250 mL dropping funnel to which is connected a silica gel drying tube. This mixture is mechanically stirred for half an hour at 0° C. in an ice bath.

Referring to step 2 in FIG. 9, after approximately 30 minutes, chlorosulfonic acid, pyridine $SO_3$ complex or a combination of the two (in this example, 167 mL of chlorosulfonic acid) is slowly added to the solution (say 1 mL/min) at 0° C. drop by drop with constant stirring over a period of about 2 hours. The mixture is stirred at 0° C. until all white fumes of HCl disappear. The solution is a white milky colour.

The ice bath is changed to a water bath, and the temperature of the water bath is gradually raised to 60° C. by a temperature-controlled heater/stirrer. At this time, xylan powder (say, 100 g in this example) is added to the mixture solution (see step 3 in FIG. 9) in portions through the side tube of the flask via long-necked funnel to give a homogenous brownish suspension. The reaction mixture is raised to 75° C. and maintained at this temperature for approximately 4 hours (see step 4 in FIG. 9), after which the water bath is removed.

The reaction mixture is cooled to room temperature (see step 5 in FIG. 9) with continuing stirring, and then sulfated xylan is precipitated by addition to (in this example) 6000 mL precooled (in an ice-bath) methanol with vigorous stirring (see step 6 in FIG. 9). The precipitate is a white, amorphous, water-soluble pyridinium salt, and the supernatant is a brown-coloured liquid. The precipitate is collected (see step 7 in FIG. 9) in this example on a Buchner funnel by water pump, the residue is washed with methanol (×3 times) to remove adhering unreacted sulfating reagent.

2.2. Conversion of the Pyridinium Salt to the Sodium Salt, as an Exemplary Arrangement of the Preferred Embodiment Referring to step 8 in FIG. 9, the residue is dissolved in distilled water (in this example, 1.5 L) with vigorous stirring, and the pH is adjusted from 3.8 to 10 (see step 9 in FIG. 9) with 6N NaOH (about 230-250 mL, in this example) in order to convert pyridinium xylan sulfate to sodium xylan sulfate.

To ensure the pH of solution is maintained at this value, it is necessary to check the pH just before rotary evaporation (step 10 in FIG. 9). After the solution is rotated and evaporated to dryness (red-brown colour) the solid residue (essentially free of pyridine and DMF) is redissolved in distilled water (see step 11 in FIG. 9) and the pH of solution is adjusted to 7.

In alternative arrangements, the pyridinium salt can be converted to other salts, by attaching to any other suitable counter ion such as an inorganic metal (e.g. Na, K, Ca, Mg, Ag) or an organic base—as described in "1.2 Conversion of the pyridinium salt to a sodium salt, as an exemplary arrangement of the preferred embodiment", above.

2.3. Hydrolysis of the Sulfated Xylan

Referring to step 12 in FIG. 9, the solution in this example is made up to 1670 mL (deep brown colour)—that is, 50 X per 3 mL, (X=original xylan in grams). This solution is transferred into a 3 L round flask in this example and fitted with a reflux condenser and heating mantle and brought to gentle boiling. Five molar $H_2SO_4$ (25 mL in this example) is added to the sulfated xylan ester solution through the condenser tube with stirring, left for approximately 35 minutes at 100° C. (see step 13 in FIG. 9). The time is an important parameter, as it determines the molecular weight of the final product. The time will need to be determined independently for each batch size. The solution is then rapidly cooled by pouring it into an ice bath. The pH of the cooled solution is 0.9-1.0. The pH is adjusted to a pH of 7 (see step 14 in FIG. 9), in this example, by taking 50-55 mL of 6N NaOH solution.

2.4. Dialysis and Drying of Hydrolysis Product

In order to keep a reasonable flow rate of permeate at a safe, constant pressure (say 15-20 psi), the hydrolysis solution concentration should be kept less than 3-4% and preferably at 1.5-2%. This provides an increased permeate collection rate, more than offsetting the increased starting volume.

Referring to steps 15 and 16 in FIG. 9, this solution needs to be filtered using a prefilter and a 0.45 µm cellulose acetate membrane, to avoid blockage of the dialysis membrane. The solution subjected to ultrafiltration using, say, a Prep/sale-TFF 6 ft2 cartridge (Millipore) which has a nominal cut off MW of 1000 Daltons, with distilled water (preferably BP purified water). The working pressure (say 15-20 psi) is maintained by an Amicon LP-1A pump for example. After 5-6× volume of distilled water (relative to the processing solution volume) has been collected as permeate, the retained solution (including washings of the system with, in this example, 500-600 mL water) is dried by rotary-evaporation typically at 50° C. under reduced pressure (see step 17 in FIG. 9). The final product (in this example, 160-180 g) is ground and put in the dessicator with $P_2O_5$ under vacuum.

2.5. Resulfation of Sulfated Xylan

Referring to step 18 in FIG. 9, the second sulfation method is similar to the first, with slight modification. A mixture of equal volumes of pyridine and DMF is mechanically stirred. In this example, 650 mL pyridine and 650 mL DMF is added to a 5000 mL two-necked round bottom flask provided with a mechanical stirrer, a 250 mL dropping funnel fitted with a silica gel tube, seated in an ice bath. When the temperature of mixed solvent is close to 0° C., 167 mL (in this example) of chlorosulfonic acid is slowly dropped into the solution over about 2 hours with continuous stirring and cooling to maintain the temperature close to 0° C.

After the addition of chlorosulfonic acid (in this example), the reaction mixture is stirred further (in this example, for a further 30 minutes). The ice bath is changed to water, and the temperature is raised to 60° C. over 1.2 to 1.5 hours. Sulfated xylan (in this example, 170 to 240 g) is added to the reaction solvent by side tube of round flask. The temperature is further raised to 75° C., and is then maintained at this temperature with stirring for about 1 hour. The heater is turned off and the hot water is drained or siphoned from the water bath. The reaction mixture is allowed to cool to room temperature with stirring. The cooled solution is poured into methanol (in this example, 6000 mL) with vigorous stirring. The precipitate is a white coloured solid.

2.6. Conversion to the Sodium Salt (as an Exemplary Arrangement) and Removal of Pyridine and DMF Referring to step 19 in FIG. 9, the precipitate is redissolved in distilled water (in this example, 1 L), with the pH being 4.1-4.2. The pH of solution is adjusted to 10. In this example, it takes about 120-140 mL of 6N NaOH solution. This solution is rotary evaporated to dryness at 50° C. (grey-white colour). The residue is dissolved in distilled water (in this example, 300 mL of distilled water) and poured into methanol (in this example, 2500-3000 mL) with vigorous stirring (see step 20 in FIG. 9). At this stage, due to the presence of a large amount inorganic salt, the precipitate can easily form lumps. The precipitate is collected by filtration under water pump suction.

As described in "1.2 Conversion of the pyridinium salt to a sodium salt, as an exemplary arrangement of the preferred embodiment", alternative arrangements include salt made with any other suitable counter ion such as an inorganic metal (e.g. Na, K, Ca, Mg, Ag) or an organic base.

2.7. Decolouring of Resulfated Xylan Using a Carbon Cartridge

The above precipitate is redissolved in distilled water (in this example, in 2 L of distilled water). The solution is deep brown. The colour can be removed by repeated circulation of solution through a carbon cartridge (e.g. an Aqua-Pure water filter APII) at room temperature for 2 hours (see step 21 in FIG. 9). The final solution becomes light yellow in colour and is rotary evaporated to dryness.

Considerable losses (up to 30%) of "good" xylan sulfate can be experienced if a carbon cartridge with low selectivity is used. It is preferable to use a good grade of activated carbon powder, in a batch process. The amount of carbon relative to the xylan sulfate is approximately 20% weight/weight.

Alternatively, decolouration can take place during fractionation, as described below.

2.8. Dialysis and Drying

Referring to step 22 in FIG. 9, the decoloured solution is filtered through a 0.45 μm cellulose acetate membrane with a prefilter. The filtrate is then desalted as described above (e.g. using a Millipore ultrafiltration system provided with a Prep/Scale™-TFF cartridge (cut off MW 1000) using purified water BP. The working pressure (10-20 psi) is maintained by an Amicon LP-1A peristaltic pump). After collecting 10× volumes of the permeate solution, the process solution is concentrated in the ultrafiltration system as high as possible (for example, 3-4%). The final solution is then dried, for example, by rotary evaporation (see step 23 in FIG. 9).

3. Selective Fractionation to Produce a Narrow Spectrum Low MW, Highly Sulfated GXS For the fractionated GXS embodiment, following completion of the double sulfation method described above, the resultant crystals are fractionated with an organic solvent such as ethanol using the procedure described below. The applicant refers to this fractionation procedure as "selective fractionation" because it uses the charge of the highly sulfated GXS molecule to "focus" the fractionation process so that precipitation occurs using the charge of the molecule in addition to molecular weight.

Using the method of selective fractionation (described below), it is possible to produce GXS compound with a consistently low molecular weight and within a narrow spectrum of weight ranges, from 1000 to 4000.

The selective fractionation method is as follows:
(a) Following on from step 23 in FIG. 9, the crystals are dissolved in H$_2$O to make a 10% solution. In this example 100 g of solid is dissolved in 1000 mL of total solution. This solution has a pH of around 5.0, unadjusted.
(b) The pH of the solution is adjusted to around 9.0 by the addition of NaOH. Adjusting the pH affects the charge of the GXS molecule and thereby its solubility in water/organic solvent mixtures.
(c) Having adjusted the pH to around 9, organic solvent (in this example, ethanol) is added in a dropwise manner (while stirring) to make up a total concentration of 40% by volume. Ethanol is added because high molecular weight fractions are the least soluble and adding an organic solvent such as ethanol will affect their solubility.
(d) The high molecular weight fractions will be the first to precipitate out of the solution. The first fraction is removed and the whole solution is then centrifuged.
(e) Organic solvent (in this example, ethanol) is added to the supernatant (which still includes the lower MW GXS) in the same manner to make up a total concentration of 45% by volume.
(f) The precipitant (second fraction) is removed and the solution again centrifuged as described in step (d) above.
(g) The steps (d) to (f) are repeated, increasing the concentration of ethanol by 5% in each cycle, up to a concentration of 70% in the final cycle.
(h) For each fraction, the precipitate is further rinsed using additional ethanol to remove as much water as possible from the crystals.

FIG. 10 is a table showing sample data obtained from size exclusion chromatography (SEC) of GXS produced using the double sulfation method described above. The second column from the left is exemplary data obtained from one batch of unfractionated GXS; the remaining columns are for fractionated GXS, using the selective fractionation method described above.

FIGS. 11 to 18 show chromatograms of the data from FIG. 10—namely, exemplary SECs of unfractionated and fractionated GSX. Each chromatogram (FIGS. 11 to 18) shows refractive index (RI) against retention time (RT). The mobile phase used was pure water with 0.05% sodium azide, with a flow rate of 0.5 mL per minute. Two Phenomenex Biosep S2000 connected in series at a temperature of 30° C. were used in the SEC experiment. The instrument was an Agilent 1100 with an RI detector, calibrated with polystyrene sulfonate standards. The sample concentration of GXS was 5 mg/mL.

Figure 11:
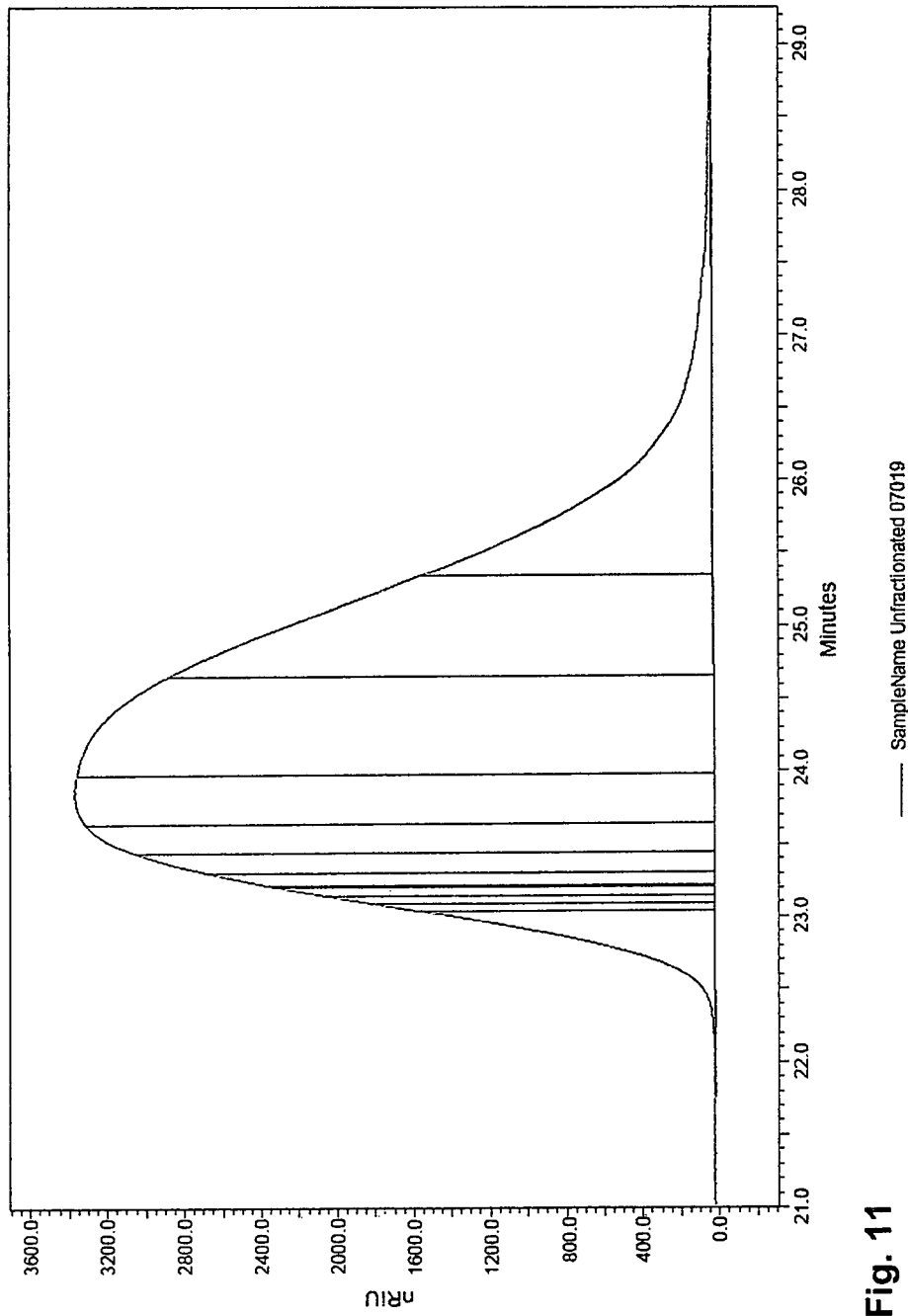
FIG. 11 is an exemplary chromatogram relating to the unfractionated GXS sample in FIG. 10.
Figure 12:
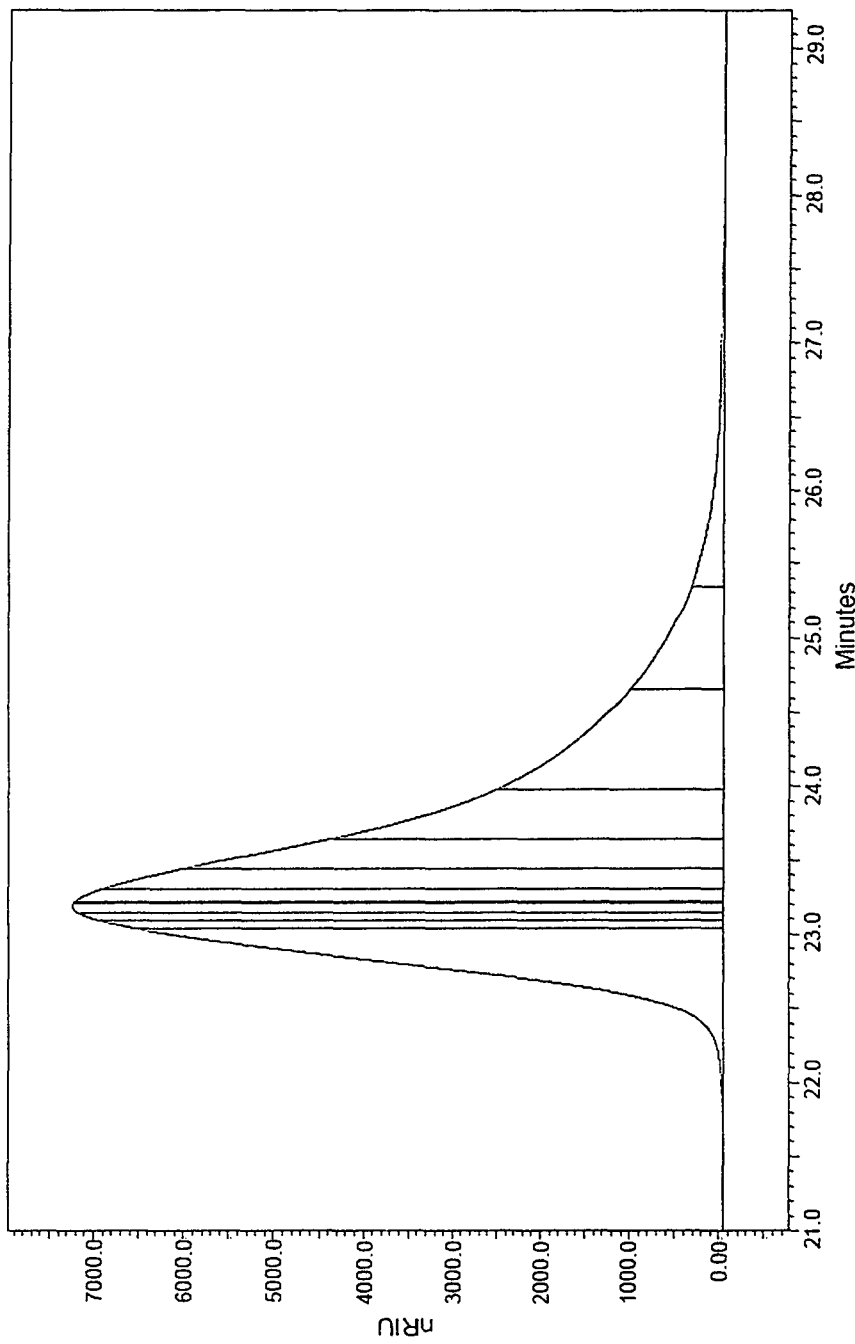
FIG. 12 is an exemplary chromatogram showing a sliced peak of a first GXS fraction obtained using 40% ethanol as the organic solvent.

Referring to second column of the table in FIG. 10 and to FIG. 11, the unfractionated GXS had an average sulfation of 18% with a peak relative MW of 3294, with the mode MW being 2759.

The first fraction (obtained using ethanol fractionation with ethanol in a concentration of 40%), gave a yield with an average sulfation of 18.1%. It can be seen from the % weight profile in the table in FIG. 10 that the first fraction removes the highest MW molecules (22% of this fraction has a relative MW higher than 10,000). The % weight profile of this fraction is illustrated in the chromatogram in FIG. 12.

Figure 13:
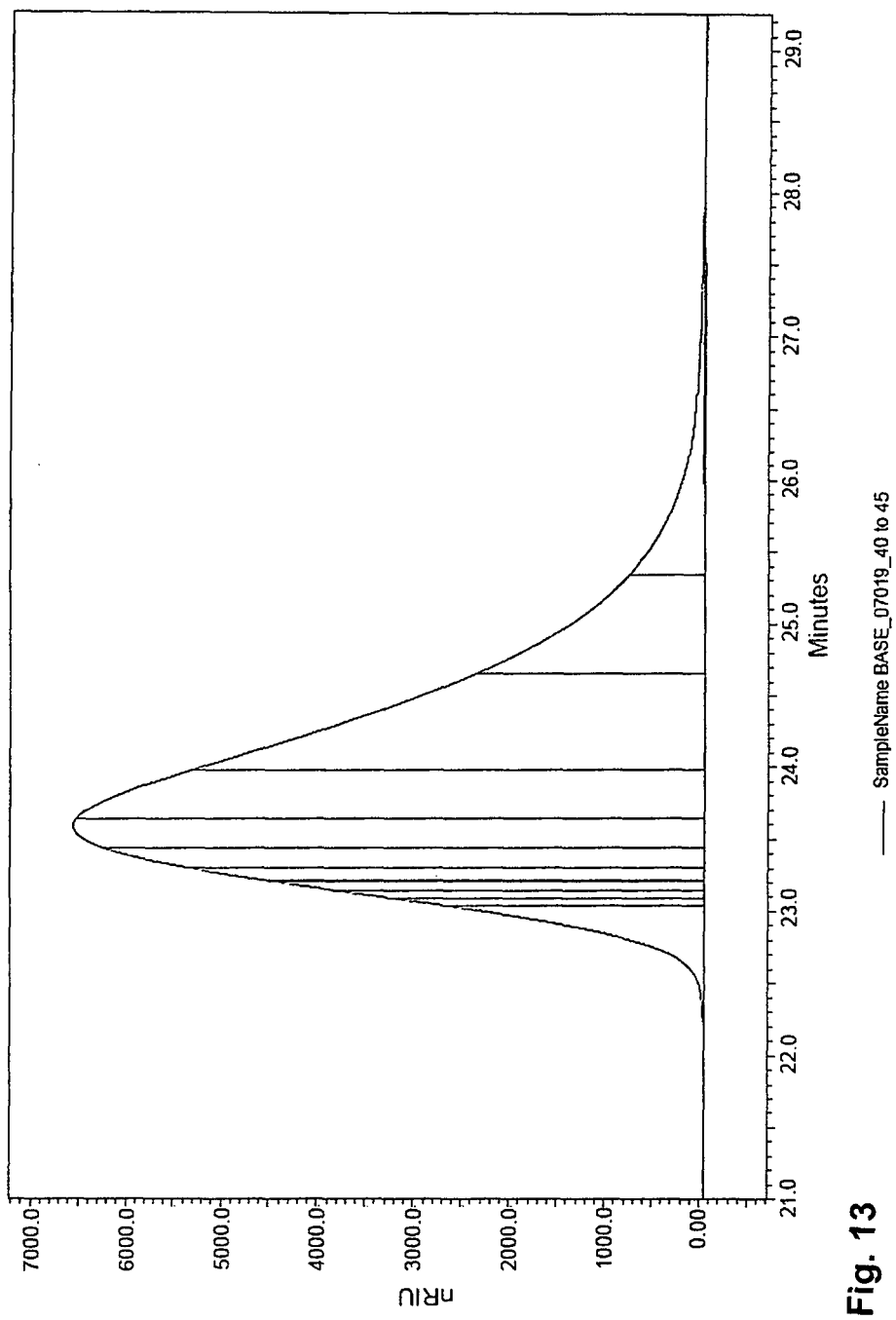
FIG. 13 is an exemplary chromatogram showing a sliced peak of a second GXS fraction obtained using 45% ethanol as the organic solvent.
Figure 14:
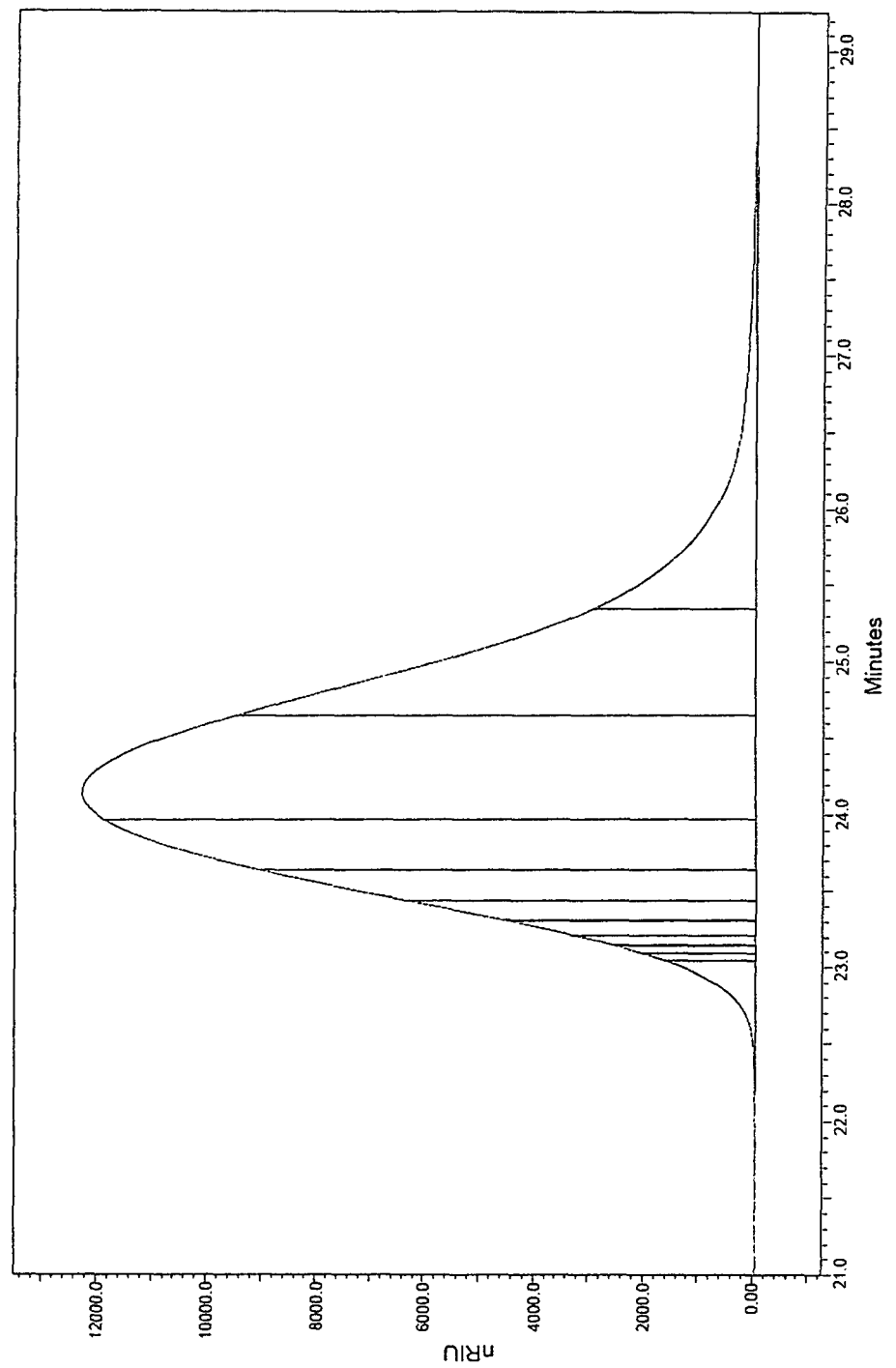
FIG. 14 is an exemplary chromatogram showing a sliced peak of a third GXS fraction obtained using 50% ethanol as the organic solvent.
Figure 15:
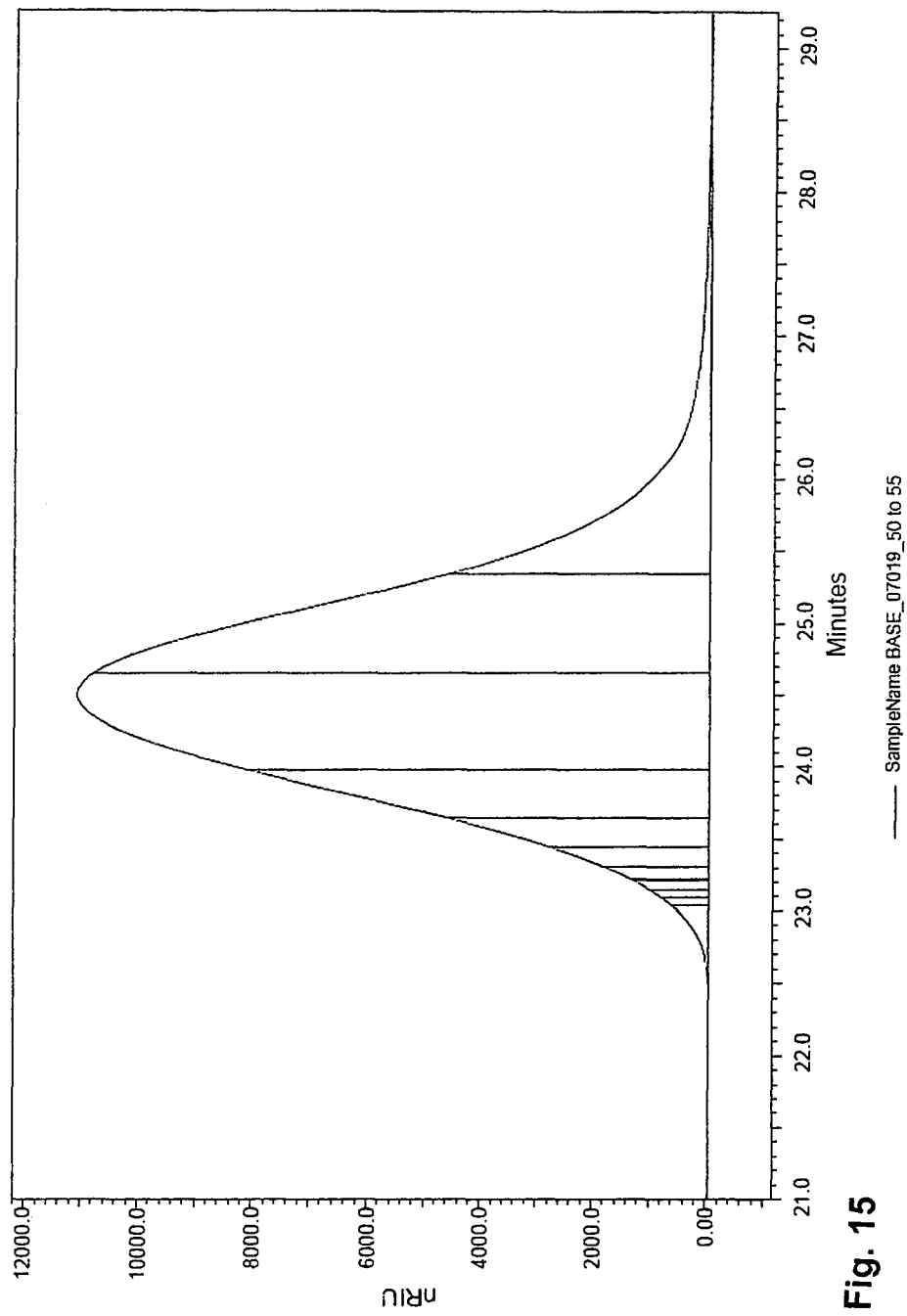
FIG. 15 is an exemplary chromatogram showing a sliced peak of a fourth GXS fraction obtained using 55% ethanol as the organic solvent.
Figure 16:
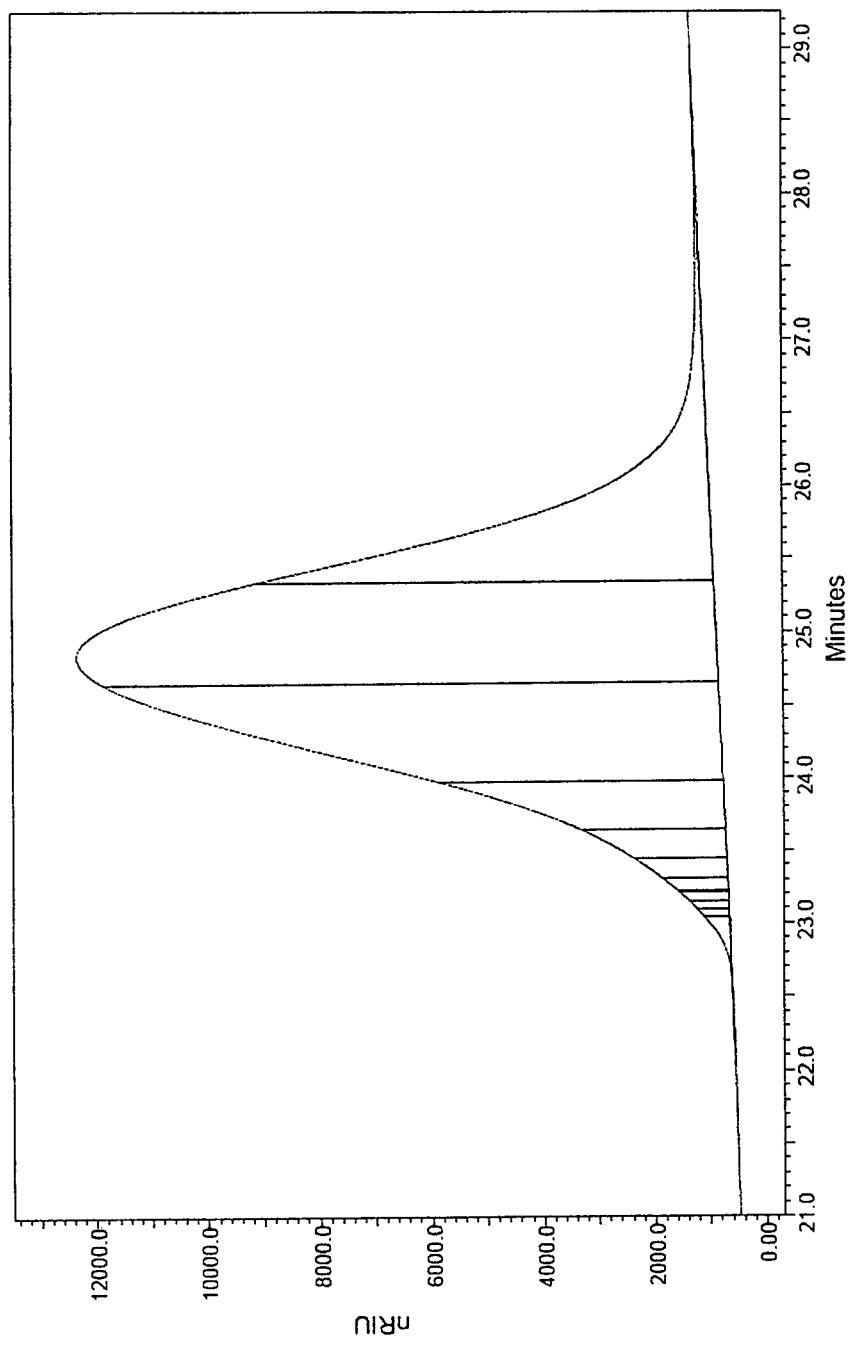
FIG. 16 is an exemplary chromatogram showing a sliced peak of a fifth GXS fraction obtained using 60% ethanol as the organic solvent.
Figure 17:
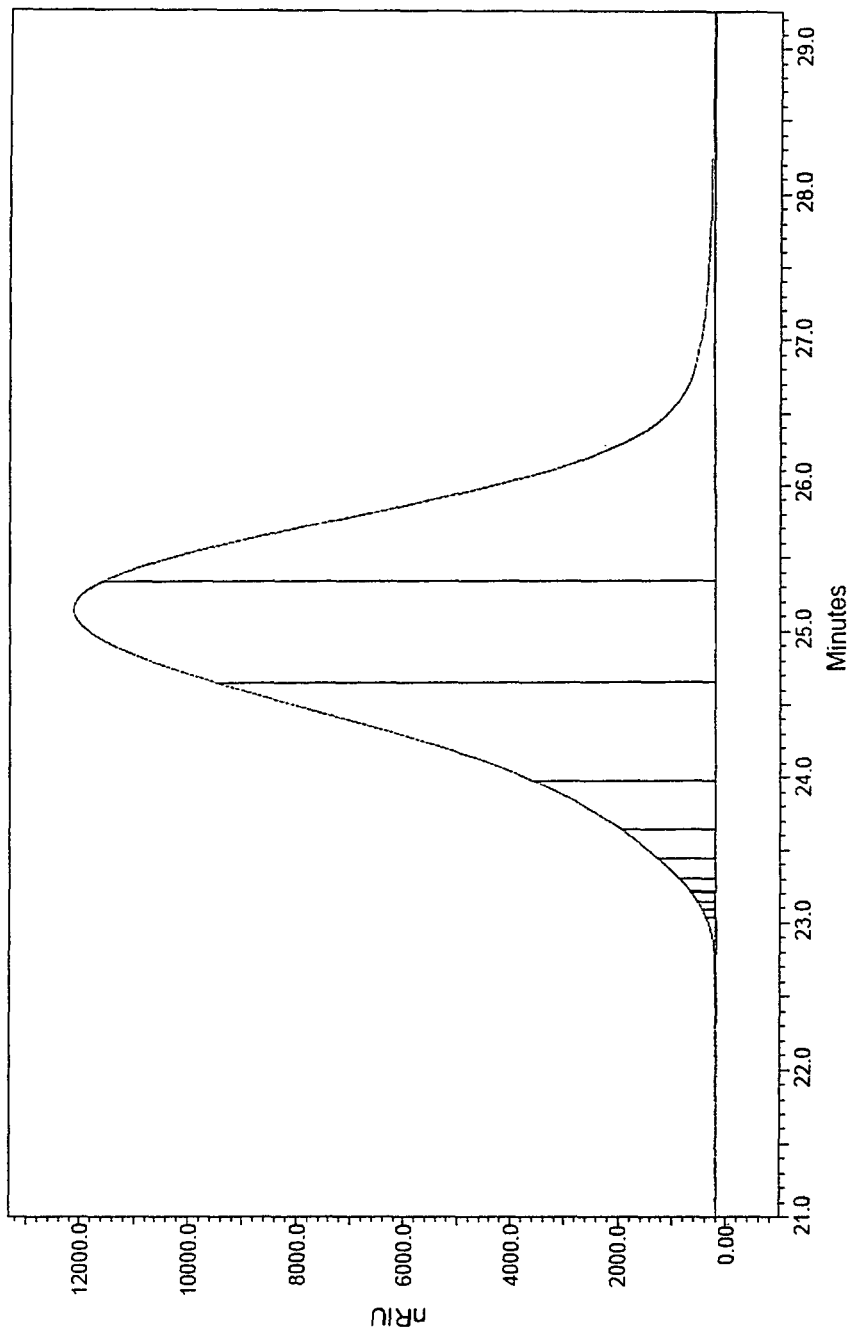
FIG. 17 is an exemplary chromatogram showing a sliced peak of a sixth GXS fraction obtained using 65% ethanol as the organic solvent.
Figure 18:
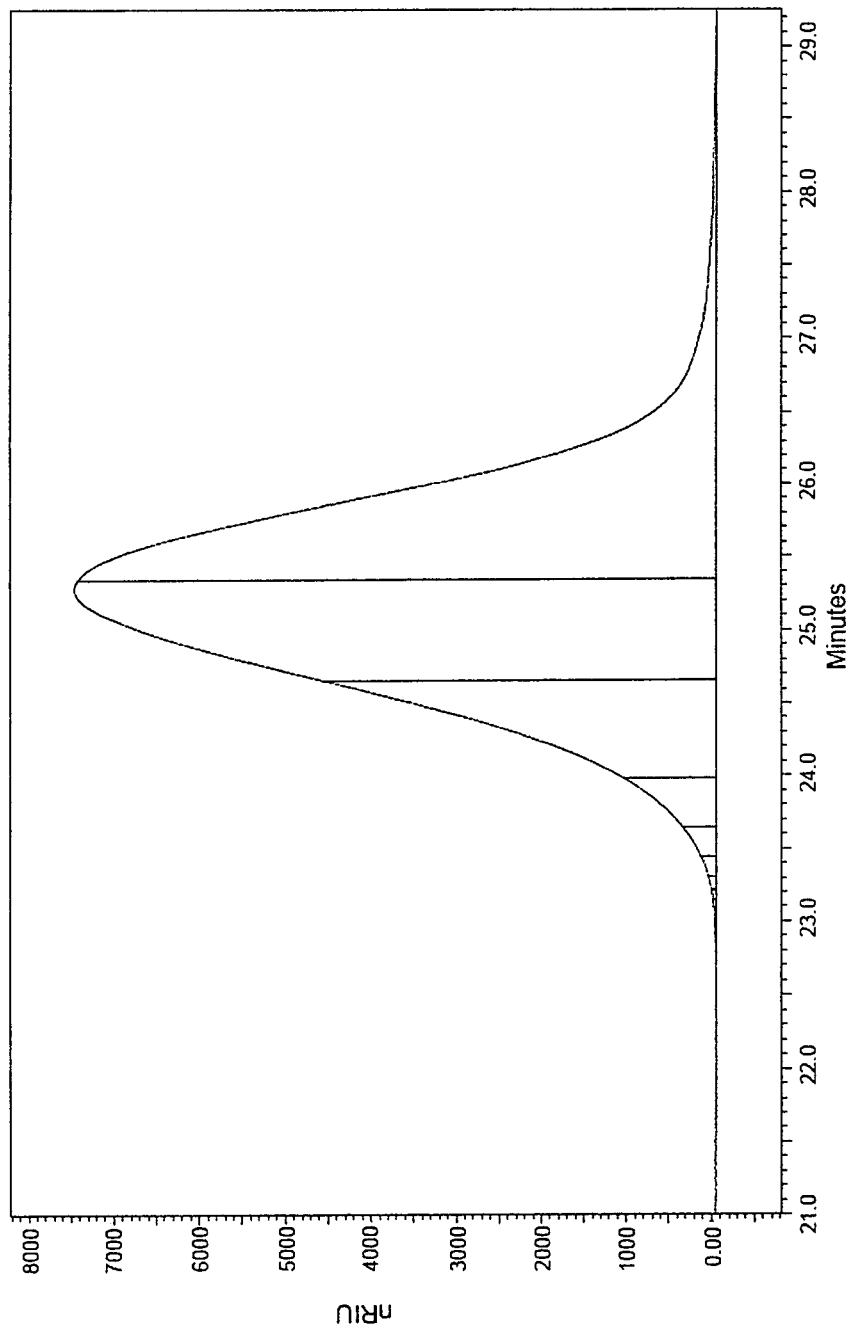
FIG. 18 is an exemplary chromatogram showing a sliced peak of a seventh GXS fraction obtained using 70% ethanol as the organic solvent.

The second fraction (in 45% ethanol), gave a yield with an average sulfation of 18.2%, with the mode MW being 2000-3000 (see FIG. 13 and the table in FIG. 10). The third fraction (in 50% ethanol), gave a yield with an average sulfation of 18.5%, with the mode MW also being 2000-3000 (see FIG. 14 and the table in FIG. 10). The fourth fraction (in 55% ethanol), gave a yield with an average sulfation of 18.4%, with the mode MW also being 2000-3000 (see FIG. 15 and the table in FIG. 10). The fifth fraction (in 60% ethanol), gave a yield with an average sulfation of 17.8%, with the mode MW being 1500-2000 (see FIG. 16 and the table in FIG. 10). The sixth fraction (in 65% ethanol), gave a yield with an average sulfation of 16.9%, with the mode MW also being 1500-2000 (see FIG. 17 and the table in FIG. 10). The seventh fraction (in 70% ethanol), gave a yield with an average sulfation of 17.1%, with the mode MW also being less than 1500 (see FIG. 18 and the table in FIG. 10).

These data indicate that second to fourth fractionation cycle gave the greatest yield of low MW, fully sulfated GXS molecules. However, yield can be affected by Mp of started unfractionated GXS. Therefore, strict control of GXS molecular weight and optimisation of manufacturing parameters are crucial to obtain high yield, desirable level of sulfation and molecular weight range.

Figure 19:
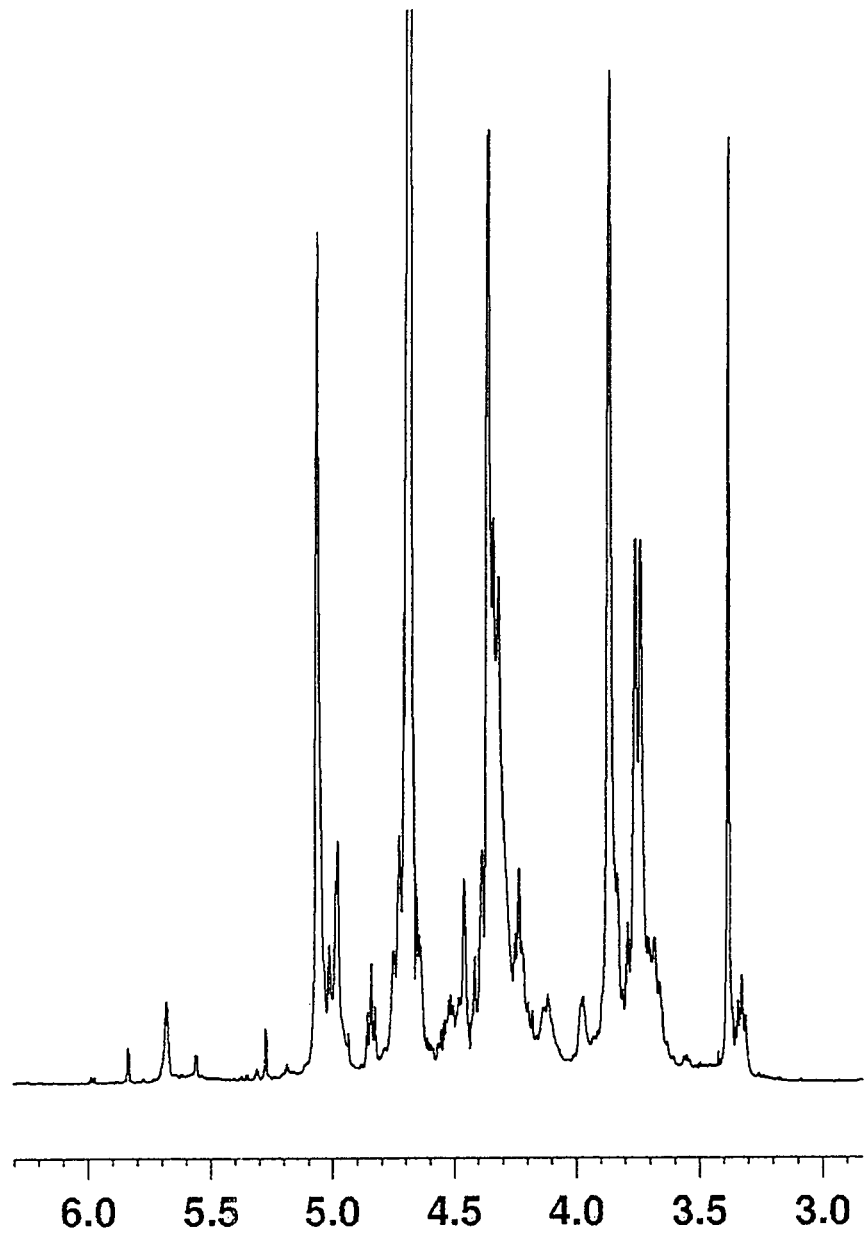
FIG. 19 is an exemplary NMR spectrum obtained from a second fractionation cycle GXS (in 45% ethanol).
Figure 20:
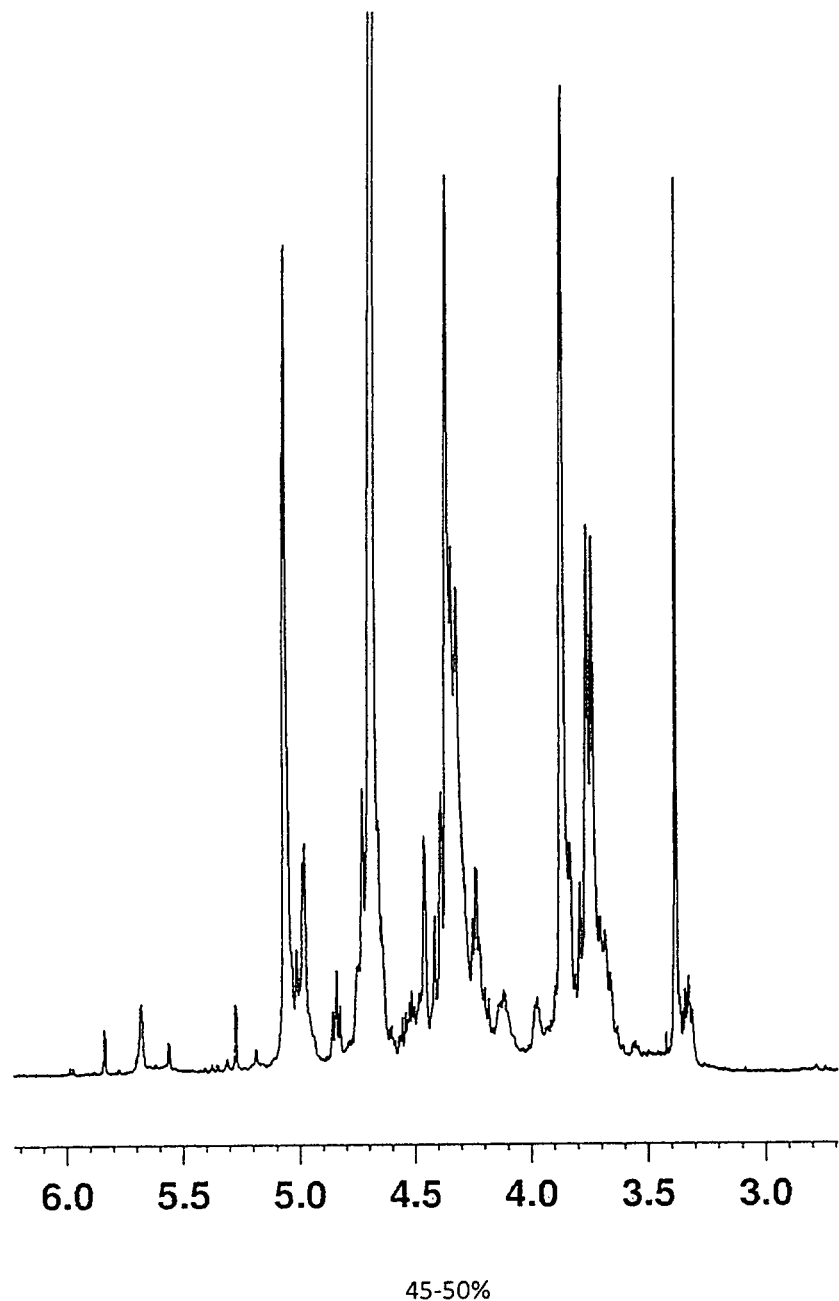
FIG. 20 is an exemplary NMR spectrum obtained from a third fractionation cycle GXS (in 50% ethanol).
Figure 21:
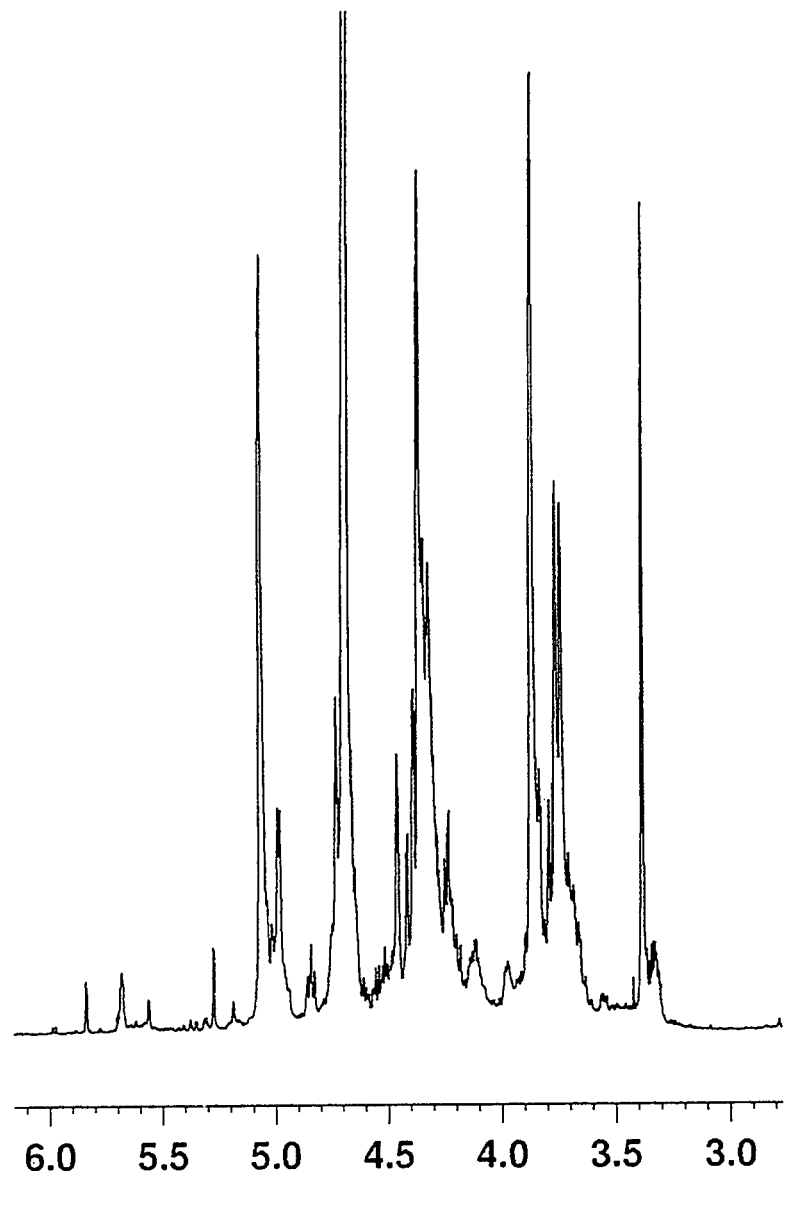
FIG. 21 is an exemplary NMR spectrum obtained from a fourth fractionation cycle GXS (in 55% ethanol).

The preferred embodiment is a mixture of GXS molecules that contains at least 10% of fully sulfated molecules, displaying the following NMR characteristics (and as shown in the exemplary NMR spectra obtained from second to fourth fractionation cycle GXS seen in FIGS. 19 to 21):
(a) a single $OCH_3$ peak of glucuronic acid around 3.3 to 3.5 ppm;
(b) a fully sulfated glucuronic acid peak around 5.2 to 5.4 ppm;
(c) at least one peak correlating to a fully sulfated right terminal xylose unit, seen at around 5.5 to 6.0 ppm; and
(d) the appearance of a single strong peak at around each of 5.1 ppm, 4.7 ppm, 4.4 ppm and 3.8 ppm, correlating to the fully sulfated xylose units.

4. Purification

The production method includes one or more ultrafiltration steps to remove impurities that can affect the quality of the end product. High performance liquid chromatography of the inventive compound, GXS, compared with prior art PPS molecules demonstrates an absence of peaks in the chromatogram tail, indicating the removal of low molecular weight impurities such as degradation products. This is achieved either by ultrafiltration or by fractionation with organic solvents, as described above.

5. Colour Removal by Fractionation

Dark colouration of the final product indicates a change of chemical structure. Colour removal therefore is important as a way for removing discoloured degradation products.

Colour removal can be achieved by perfusion with hydrogen peroxide or chlorine, as described in step 1.3 above, or with charcoal as described in step 2.7. These methods of colour removal have proved to be a most difficult step in production.

A preferred embodiment of the production method utilises selective organic solvent fractionation as a means for colour removal, because lowest molecular weight fractions are darkest in appearance. This has the advantages of not involving additives and minimising the steps and costs in production.

Method of Use of GXS: a Preferred Embodiment

The highly sulfated, low molecular weight GXS of the present invention is administered parenterally in a preferred embodiment (including by intramuscular, subcutaneous or intravenous injection). Delivery may be by traditional hypodermic syringe or by a pen-like delivery device that enables dial-up dosing or pre-loading with a single-dose cartridge of GXS aqueous solution.

Alternatively, the GXS may be a sustained- or controlled-release formulation administered by depot injection. This may have practical use in animals not currently treated for certain conditions (such as joint inflammation and other disorders).

An alternative embodiment may be administered orally, depending on the clinical condition being treated. This may have more practical application for formulations containing fractionated GXS rather than unfractionated GXS, since research suggests bioavailability of the fractionated compound is better than for the unfractionated compound.

Research suggests that GXS has a role in the treatment of a wide range of clinical conditions in animals, including humans, food-producing animals, and companion animals (such as feline, canine and equine). The range of conditions in which GXS may have a role in treatment include:
(a) non-infective inflammatory diseases such as osteoarthritis;
(b) ischaemia;
(c) cancer;
(d) the control and treatment of virus diseases, including immunodeficiency virus (such as HIV/AIDS or feline immunodeficiency virus (FIV)) and equine flu;
(e) interstitial cystitis;
(f) Crohn's disease;
(g) ulcerative colitis;
(h) Reiter's syndrome;
(i) prion diseases such as transmissible spongiform encephalopathy (TSE), bovine spongiform encephalopathy (BSE) and Creutzfeldt-Jakob disease (CJD) and its iatrogenic variant vCJD in humans;
(j) haematomas;
(k) haemorrhoids, frostbite, burns; and
(l) multiparameter illnesses such as thrombosis and atherosclerosis.

Dosages ranging from 1 mg/kg to 10 mg/kg have been reported in the literature for the use of prior art PPS in various conditions. Experiments indicate that dosing in the range from around 1 mg/kg to 20 mg/kg for GXS would be of clinical benefit in various conditions.

For example, GXS is one of a new generation of pharmaceuticals referred to as Disease Modifying Osteoarthritis Drugs (DMOADs). GXS stimulates proteoglycan synthesis in the cells of arthritic cartilage, and reduces the loss of proteoglycan in the cartilage by the inhibiting enzymes which degrade cartilage, thereby modifying the disease process. In one arrangement of a preferred embodiment, GXS is a means for treating degenerative joint disease such as osteoarthritis and is clinically effective in repairing joint damage.

In another arrangement of the preferred embodiment, GXS is a means for prophylaxis in degenerative joint disease such as osteoarthritis and is clinically effective in preventing joint damage.

An exemplary method of use includes a dosing regimen of around 1 to 10 mg/kg given by intramuscular or subcutaneous injection, once a week for at least four weeks.

The clinical applications of the preferred embodiment are based on experiments using dosage regimens of around 3 mg/kg/week for up to a 12 week course in adult and yearling thoroughbred horses. The experiments have been conducted using unfractionated GXS with 18% or greater sulfation. The studies show statistically significant improvement in treatment and prevention of degenerative joint disease such as osteoarthritis. This was measured by assessing clinical lameness scores and levels of serum biomarkers such as epitope CS846. This epitope is an indicator of proteoglycan aggrecan synthesis, which occurs during repair of cartilage. In adult horses receiving intramuscular GXS, an increase in CS846 levels ($p=0.01$) was seen over 12 weeks, indicating increased repair in the joint.

Yearlings exhibit naturally high levels of CS846 because of rapid growth and constant joint remodelling in this age group.

Yearlings that received intramuscular GXS (weekly doses of 3 mg/kg IM for up to 12 weeks) showed a significant decrease in CS846 levels (p=0.05) over 12 weeks, indicating a protective effect against joint damage from Stage 1 disease (onset of osteoarthritis with no visible clinical signs).

Prior art research in horses using known PPS at a dose of 3 mg/kg and measuring clinical effectiveness in osteoarthritis (also by measuring epitope CS846 levels) failed to show a statistically significant effect. This confirms the applicant's conclusion that GXS (fractionated or unfractionated) is a different chemical entity to prior art PPS extracted from xylan.

A Preferred Embodiment of a GXS Formulation

In a preferred embodiment, the active ingredient GXS is formulated into aqueous solution for parenteral injection (including intramuscularly, subcutaneously or intravenously).

In one arrangement, the injectable formulation includes a suitable antioxidant to enable the aqueous formulation to remain substantially stable (that is to resist discolouration and degradation) without refrigeration. Patent WO 2007/123800 claims a PPS formulation with "an antioxidant in the group metabisulfite, sodium bisulfate and ascorbate in a concentration of about 0.02% w/v to about 5.0% w/v" is stable without refrigeration. However, experiments by the applicant revealed that many antioxidants are not effective on GXS in an aqueous solution. For example, ascorbate does not act as an anti-oxidant, since in its presence the GXS still dissociates and becomes discoloured. This finding supports a conclusion that GXS is a distinct entity to prior art PPS extracted from xylan.

Experiments by the applicant found that only sulfur-containing antioxidants are suitable for preventing degradation and discolouration of an injectable GXS formulation at ambient room temperature for at least seven months. Table 2 below lists examples of sulfur-containing antioxidants found to be suitable for this use.

TABLE 2

Examples of sulfur-based antioxidants found to be suitable

| Name | CAS no. | Exemplary effective concentration * |
|---|---|---|
| Sodium metabisulfite | 7681-57-4 | 0.5% by weight/volume |
| Sodium bisulfite ACS Reagent | Mix of 7681-57-4 and 7631-90-5 | 0.5% by weight/volume |
| Sodium hydroxymethane sulfonate | 149-44-0 | 1% by weight/volume |
| Formaldehyde-sodium bisulfate | 870-72-4 | 1% by weight/volume |

* To achieve substantial stability of GXS injectable formulation

The preferred embodiment may be packaged as an injectable formulation for delivery by traditional hypodermic syringe or delivery by a pen-like delivery device that enables dial-up dosing or pre-loading with a single-dose cartridge of GXS aqueous solution.

In a further embodiment, the GXS is a sustained- or controlled-release formulation administered by depot injection. This formulation may suit use in animals not currently under regular veterinary supervision—such as dairy cattle for whom, say, decreased mobility arising from joint pain can affect overall health, including milk production and reproduction. As cattle are not generally required to move quickly, joint pain and inflammation in such animals may go unattended. This is in contrast to animals such as thoroughbred horses or dogs that need maximal mobility and are under very regular attendance by vets. A slow-release formulation would enable animals that may go untreated (e.g. for inflammatory joint conditions) to be treated with GXS without requiring regular (say, weekly) attendance by a vet, which may have both important production and animal welfare implications.

A further embodiment is a solid unit dosage formulation of GXS for oral administration; however, as bioavailability of unfractionated GXS is poor when taken orally, the dosage required for therapeutic effect may make oral administration of unfractionated GXS unsuitable for some clinical indications. Research suggests that bioavailability of fractionated GXS would be better than bioavailability of unfractionated GXS when taken orally. Therefore, an oral formulation of fractionated GXS may have wider clinical use than oral formulations of unfractionated GXS or of prior art unfractionated sulfate esters such as PPS (which are currently indicated for interstitial cystitis in humans).

Examples of arrangements of the preferred embodiment (GXS in aqueous solution for parenteral administration) may comprise GXS in a concentration of about 0.1 to about 500 mg/mL.

By way of example, for a 100 mg/mL solution with a 10 mL pack size, the formulation may include:
 (a) around 100 mg GXS;
 (b) around 10 mg benzyl alcohol as preservative
 (c) around 0.8 mg citric acid anhydrous as buffer;
 (d) around 15 mg trisodium citrate dehydrate as buffer;
 (e) to 1.0 mL water for injection as the vehicle.

A second exemplary arrangement of the preferred embodiment is a 250 mg/mL solution with a 6 mL pack size. The formulation may include:
 (a) around 250 mg GXS;
 (b) around 10 mg benzyl alcohol as preservative
 (c) around 2 mg citric acid anhydrous as buffer;
 (d) around 38 mg trisodium citrate dehydrate as buffer;
 (e) to 1.0 mL water for injection as the vehicle.

For room temperature formulations of the above exemplary arrangements, a suitable antioxidant is added in an effective concentration, examples of which are provided in Table 2. Optionally, the head space in the room temperature formulations may also be replaced with nitrogen.

An Alternative Embodiment: GXS as a New or Improved Antioxidant

Experiments by the applicant show that GXS is oxidised more readily than some common antioxidants (BHA, BHT, lipoic acid, glutamic acid, gentisic acid, methyl sulfonyl methane, malic acid, nicotinic acid, ascorbates). This finding indicates that GXS has excellent antioxidant properties in its own right. Scientific literature indicates that the $OSO_3$ at position 1 (such as at the right terminal xylose unit in GXS) is generally highly labile, hence GXS would be oxidized in preference to ascorbic acid (or the other antioxidants listed above).

This conclusion is supported by the finding (discussed earlier) that only sulfur-containing antioxidants are suitable for preventing degradation of GXS, because the sulfur in the antioxidant is preferentially oxidised to the $OSO_3$ of the right terminal or other carbohydrate units in GXS.

In a preferred embodiment, GXS is suitable for use as an antioxidant, including in preparations for clinical use.

Although the invention has been described with reference to specific examples, it will be appreciated by those skilled in the art that the invention may be embodied in many different other forms.

The invention claimed is:

1. A method for the production of sulfated glycan molecules, the method comprising:
    (a) hydrolysis of xylan sulfates; followed by
    (b) sulfation, wherein the sulfation results in xylan sulfates having an increased sulfur content of 17% to 21.9% based upon the weight of the sodium salt of the xylan sulfates.

2. A method for the production of sulfated glycan molecules, the method comprising:
    (i) performing sulfation of xylan to provide partially sulfated xylan sulfates;
    (ii) performing hydrolysis of the partially sulfated xylan sulfates to provide hydrolysed xylan sulfates;
    (iii) performing sulfation of the hydrolysed xylan sulfates to provide xylan sulfates having an increased sulfur content of 17% to 21.9% based upon the weight of the sodium salt of the xylan sulfates.

3. A method for the production of sulfated glycan molecules, the method comprising:
    (a) performing sulfation of xylan, by reaction with:
        (i) pyridine chlorosulfonic acid complex in DMF;
        (ii) pyridine $SO_3$ complex in DMF; or
        (iii) a mixture of (i) and (ii) above,
        to produce pyridinium xylan sulfates;
    (b) replacing pyridinium with a counter ion to form non-pyridinium xylan sulfate salts, followed by removal of pyridinium and DMF;
    (c) performing acid hydrolysis of the non-pyridinium xylan sulfate salts; and
    (d) performing sulfation of the non-pyridinium xylan sulfate salts obtained following step (c) as described in step (a), followed by conversion to sodium salts and removal of the pyridine and DMF.

4. The method of claim 3, further comprising performing ultrafiltration of the non-pyridinium xylan sulfate salts to remove inorganic impurities and degradation products.

5. The method of claim 3, wherein the counter ion is an inorganic metal or an organic base.

6. The method of claim 4, wherein the counter ion is an inorganic metal or an organic base.

7. The method of claim 1, wherein the sulfated glycan molecules comprise one or more linear 1-4 conjugated beta-D-xylose units and at least one 4-O-methyl-beta-D-glucuronic acid unit attached to carbon-2 of every about eight to about ten xylose units.

8. The method of claim 2, wherein the sulfated glycan molecules comprise one or more linear 1-4 conjugated beta-D-xylose units and at least one 4-O-methyl-beta-D-glucuronic acid unit attached to carbon-2 of every about eight to about ten xylose units.

9. The method of claim 3, wherein the sulfated glycan molecules comprise one or more linear 1-4 conjugated beta-D-xylose units and at least one 4-O-methyl-beta-D-glucuronic acid unit attached to carbon-2 of every about eight to about ten xylose units.

10. The method of claim 1, wherein in step (b) the sulfation results in xylan sulfates having 18% to 21.9% sulfur based upon the weight of the sodium salt of the xylan sulfates.

11. The method of claim 2, wherein the xylan sulfates have 18% to 21.9% sulfur based upon the weight of the sodium salt of the xylan sulfates.

* * * * *